(12) United States Patent
Rosenberger et al.

(10) Patent No.: US 8,747,860 B2
(45) Date of Patent: Jun. 10, 2014

(54) METHODS AND COMPOSITIONS TO MODULATE ANTIVIRAL AND IMMUNE ACTIVITY RESPONSES

(75) Inventors: Carrie M. Rosenberger, San Francisco, CA (US); Alan A. Aderem, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 0 days.

(21) Appl. No.: 13/542,581

(22) Filed: Jul. 5, 2012

(65) Prior Publication Data

US 2013/0022602 A1 Jan. 24, 2013

Related U.S. Application Data

(60) Provisional application No. 61/505,043, filed on Jul. 6, 2011.

(51) Int. Cl.
| | |
|---|---|
| *A61K 39/12* | (2006.01) |
| *C12N 7/00* | (2006.01) |
| *C12N 7/02* | (2006.01) |
| *C12N 7/04* | (2006.01) |

(52) U.S. Cl.
USPC ............ 424/204.1; 435/235.1; 435/236; 435/239; 435/325

(58) Field of Classification Search
None
See application file for complete search history.

(56) References Cited

FOREIGN PATENT DOCUMENTS

| WO | WO-2006/137941 | 12/2006 |
| WO | WO-2009/152181 | 12/2009 |
| WO | WO-2011/072390 | 6/2011 |

OTHER PUBLICATIONS

Rosenberger et al. miR-144 is a negative regulator of the host antiviral response. The Journal of Immunology, Apr. 2011, 186,158.10, Meeting Abstract Supplement. Retrieved on Aug. 13, 2013. Retrieved from the Internet <URL:jimmunol.org/cgi/content/meeting_abstract/186/1_MeetingAbstracts/158.10>.*
Schultz-Cherry et al. Mink lung epithelial cells: unique cell line that supports influenza A and B virus replication. Journal of Clinical Microbiology, 1998, vol. 36, p. 3718-3720.*
Virology-Introduction. Hunt. University of South Carolina School of Medicine. 2005, retrieved on Aug. 22, 2013. Retrieved from the Internet <URL:pathmicro.med.sc.edu/mhunt/intro-vir.htm>.*
Liu et al. Modulation of T cell cytokine production by miR-144 with elevated expression in patients with pulmonary tuberculosis. Molecular Immunology, 2011, vol. 48, p. 1084-1090.*
Aderem, "Systems Influenza Program Highlights", 3rd Annual Systems Biology Programmatic and SBWG Meeting (2011), retrieved from the Internet on Oct. 3, 2012.
Chassin et al., "miR-146a Mediates Protective Innate Immune Tolerance in the Neonate Instestine", Cell Host & Microbe (2010) 8:358-368.
Dore et al., "A GATA-1-regulated microRNA locus essential for erythropoiesis", PNAS (2008) 105(9):3333-3338.
Ellis-Connell et al., "Cellular MicroRNAs 200b and 429 Regulate the Epstein-Barr Virus Switch between Latency and Lytic Replication", Journal of Virology (2010) 84(19):10329-10343.
Fu et al., "Mir-144 selectively regulates embryonic a-hemoglobin synthesis during primitive erythropoiesis", Blood (2009) 113(6):1340-1349.
Grassman et al., "The roles of microRNAs in mammalian virus infection", Biochimica et Biophysica Acta (2008) 1779(11):706-711.
Heinig et al., "A trans-acting locus regulates an anti-viral expression network and type Idiabetes risk", Nature (2010) 467(7314):460-464.
Hunt, "Basic Virology: Definitions, Classification, Morphology and Chemistry", Microbiology and Immunology On-line, accessed Aug. 23, 2013.
International Search Report and Written Opinion for PCT/US2012/045812, mailed Oct. 9, 2012, 14 pages.
Konno et al., "TRAF6 Establishes Innate Immune Responses by Activating NF-[kappa]B and IRF7 upon Sensing Cytosolic Viral RNA and DNA", PLOS One (2009) 4(5):e5674.
Liu et al., "Modulation of T cell cytokine production by miR-144 with elevated expression in patients with pulmonary tuberculosis", Molecular Immunology (2011) 48:1084-1090.
Papapetrou et al., "A Genetic for Single and Combinatorial Analysis of miRNA Function in Mammalian Hematopoietic Stem Cells", Stem Cells (2010) 28:287-296.
Rosenberger et al., "miR-144 is a negative regulator of the host antiviral response", The Journal of Immunology (2011) 186:158.10 (Meeting Abstract Supplement).
Schultz-Cherry et al., "Mink Lung Epithelial Cells: Unique Cell Line That Supports Influenza A and B Virus Replication", Journal of Clinical Microbiology (1998) 36(12):3718-3720.
Skalsky and Cullen, "Viruses, microRNAs, and Host Interactions", Annu. Rev. Microbiol. (2010) 64:123-141.
Xiao and Rajewsky, "MicroRNA Control in the Immune System: Basic Principles", Cell (2009) 136:26-36.
Zhang et al., "Synergistic effects of the GATA-4-mediated miR-144/451 cluster in protection against simulated ischemia/reperfusion-induced cardiomyocyte death", Journal of Molecular and Cellular Cardiology (2010) 49(5):841-850.

* cited by examiner

*Primary Examiner* — Louise Humphrey
(74) *Attorney, Agent, or Firm* — Morrison & Foerster LLP

(57) ABSTRACT

The invention is directed to an improved method to manufacture virus for use in vaccine by culturing infected cells that have been modified to overexpress miR-144. The invention is also directed to manipulating the activity or level of miR-144 in subjects in order to modulate the antiviral and immune response systems.

4 Claims, 28 Drawing Sheets

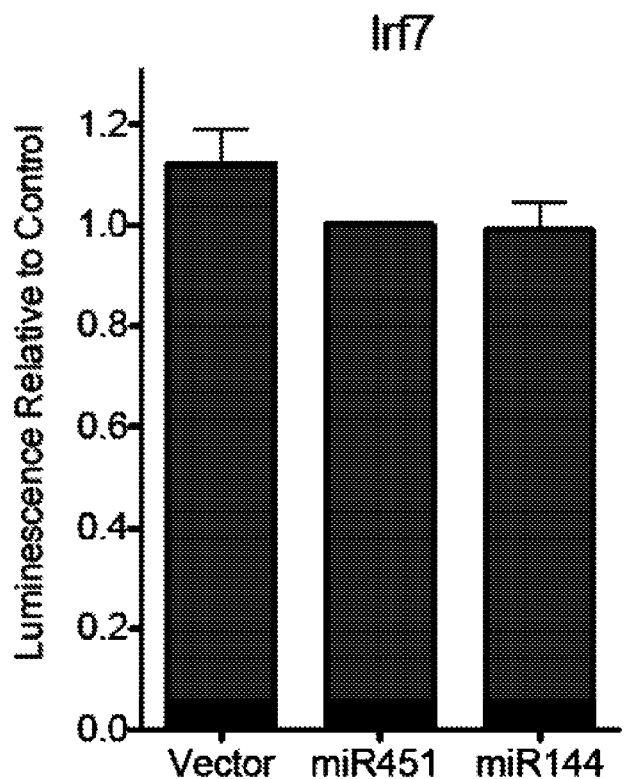
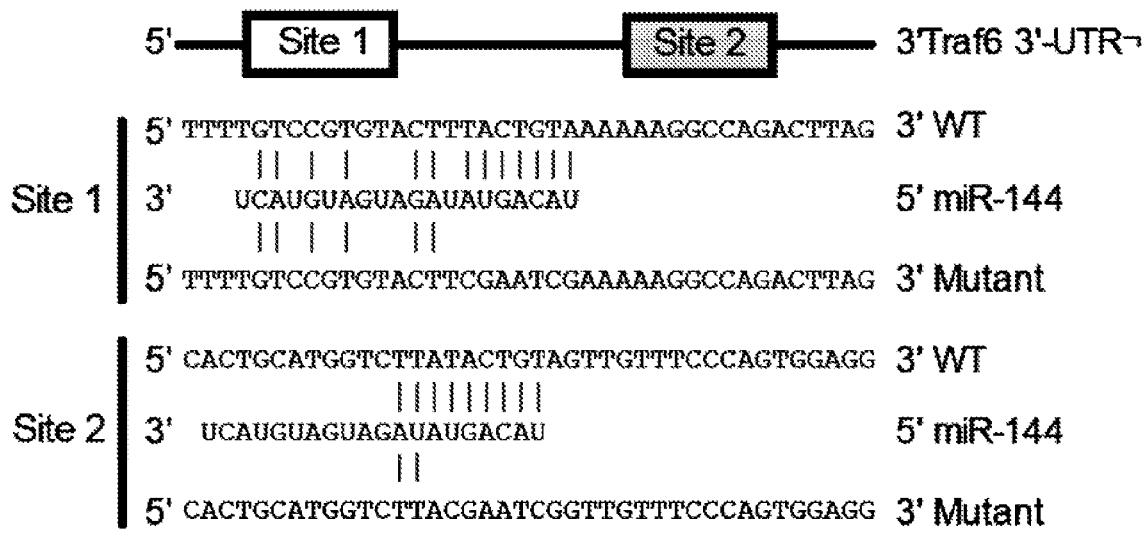
Figure 4A
Figure 4B

METHODS AND COMPOSITIONS TO MODULATE ANTIVIRAL AND IMMUNE ACTIVITY RESPONSES

CROSS-REFERENCE TO RELATED APPLICATION

This application claims priority from U.S. provisional application 61/505,043 filed 6 Jul. 2011. The contents of this document are incorporated herein by reference.

STATEMENT OF RIGHTS TO INVENTIONS MADE UNDER FEDERALLY SPONSORED RESEARCH

This work was supported by NIH Serial No. 2722 00800058C grant from the National Institutes of Health. The U.S. government has certain rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 655652003900Seqlist.txt, date recorded: 29 Aug. 2012, size: 1,785 bytes).

FIELD OF THE INVENTION

The invention relates to modulating responses of subjects to infection, in particular viral infection, as well as modulating the immune system generally. The invention is directed to manipulating the activity or level of miR-144 in subjects.

BACKGROUND ART

MicroRNAs (miRNAs) are a phylogenetically conserved class of post-transcriptional regulators that are excellent candidates for finely tuning immune responses. These small (20-25 nucleotide) non-coding RNAs bind to target mRNAs by base-pairing to effect mRNA degradation or translational repression. The ability of microRNAs to shape host-virus interactions has been reviewed in Xiao, C., et al., *Cell* (2009) 136:26 and Skalsky, R. L., et al., *Annu. Rev. Microbiol.* (2010) 64:123. For example, miR-122 directly interacts with the hepatitis C viral genome to stimulate translation and aid viral growth, and cellular or viral-encoded microRNAs directly bind to viral mRNA transcripts to inhibit viral growth of HCV or promote latency of herpes virus and HIV. However, little is understood of the mechanisms underlying how host miRNAs shape antiviral resistance by controlling innate signaling pathways.

The present invention is based in part on our finding that miR-144 is a negative regulator of a module of antiviral interferon-induced genes controlled by TRAF6 and IRF7 which fine-tune the capacity of epithelial cells to restrict viral replication. miR-144 (and miR-451) are clustered on mouse chromosome 11, and are co-expressed as one pre-miR transcript in erythroid cells where they bind to unique sequences in target genes to play non-redundant roles in lineage differentiation (Papapetrou, E. P., et al., *Stem cells* (2010) 28:287; Dore, L. C., et al., *Proc. Natl. Acad. Sci. USA* (2008) 105: 3333; and Fu, Y. F., et al., *Blood* (2009) 113:1340). It has been shown that constitutive expression levels of miRNAs provide a mechanism for maintaining mucosal homeostasis (Chassin, C., et al., *Cell Host Microb* (2010) 8:358).

The present invention is also based on the surprising finding that cultured cells that overexpress miR-144 offer greatly increased viral titers when then infected with virus. A variety of viral strains show this greatly enhanced production in such cells. This offers a much more convenient way to prepare viral vaccines, therefore, than methods currently employed which are quite expensive and cumbersome. Currently employed methods most commonly use fertilized eggs to culture the viruses. In this process, eggs containing embryos are infected with virus and incubated for 2-3 days before killing the embryo and physically removing the allantoic fluid. This procedure clearly is labor-intensive as well as awkward. These operations can be automated, but this requires expensive equipment.

Alternatively, cell lines such as Vero cells, MDCK cells and PER.C6® cells have been employed but these methods do not produce large quantities of virus and they, too are expensive. In general, the recovered viruses are processed by "splitting" or inactivating the harvested virus in a manner similar to the virus harvested from fertilized eggs. In an alternative to inactivating the viruses, the virus may have been attenuated by genetic modification. These standard techniques are less than satisfactory due to costs and inefficiency.

DISCLOSURE OF THE INVENTION

The ability of miR-144 to enhance the production of virus in cultured cells offers a more practical alternative to vaccine production from those techniques currently used.

Thus, in one aspect, the invention is directed to a method to produce virus for use as a component in an antiviral vaccine which method comprises culturing host cells that have been modified to overexpress miR-144 and also infected with said virus, and recovering the virus from the cells.

In another aspect, the invention derives from the discovery by applicants that antiviral responses are diminished in subjects in response to miR-144, a micro-RNA that has not been implicated in viral defense. Further, applicants have found that the mechanism for interaction of miR-144 is directly with TRAF6, which in turn interacts with IRF7 to activate transcription of a group of genes with known antiviral activities. Because the proteins encoded by these genes are involved in the immune response generally, methods to modulate the levels or activity of miR-144 are useful in a wider context than viral defense since immune responses are important in respect to any infection, with respect to inflammation, and with respect to autoimmune diseases.

Thus, in another aspect, the invention is directed to a method to modulate the antiviral response in a subject which method comprises either (a) increasing said antiviral response by decreasing the level or activity of miR-144 or (b) decreasing the antiviral response by increasing the level or activity of miR-144.

In still another aspect, the invention is directed to a method to modulate the immune system of a subject which comprises either (a) increasing the level of immune activity by decreasing the level or activity of miR-144 in said individual or (b) decreasing immune activity by enhancing the level or activity of miR-144 in said subject.

The invention is also directed to compositions useful in carrying out these methods.

BRIEF DESCRIPTION OF THE DRAWINGS

FIGS. 1A-1F show that enhanced levels of miR-144 are present in cells significant in viral infection and that enhanced levels of miR-144 result in increased viral loads and viral expression as compared to cells or mice with lower levels of miR-144 when infected with relevant chemical isolates of virus.

FIGS. 2A-2B show the results if experiments that demonstrate increased viral NP protein expression in human cells expressing miR-144, when infected with relevant clinical viral isolates.

FIGS. 3A-3C show the effect of miR-144 on expression levels of various genes. FIGS. 3D-3H demonstrate the correlation between miR-144 and IRF7. FIG. 3I shows the impact of miR-144 on viral infection.

FIGS. 4A-4D (SEQ ID NOS:4-8) demonstrate that the effect of miR-144 is directed to TRAF6.

FIGS. 5A-5D demonstrate that the interrelationship of miR-144 with IRF7 is mediated by TRAF6.

MODES OF CARRYING OUT THE INVENTION

Figure 1A:
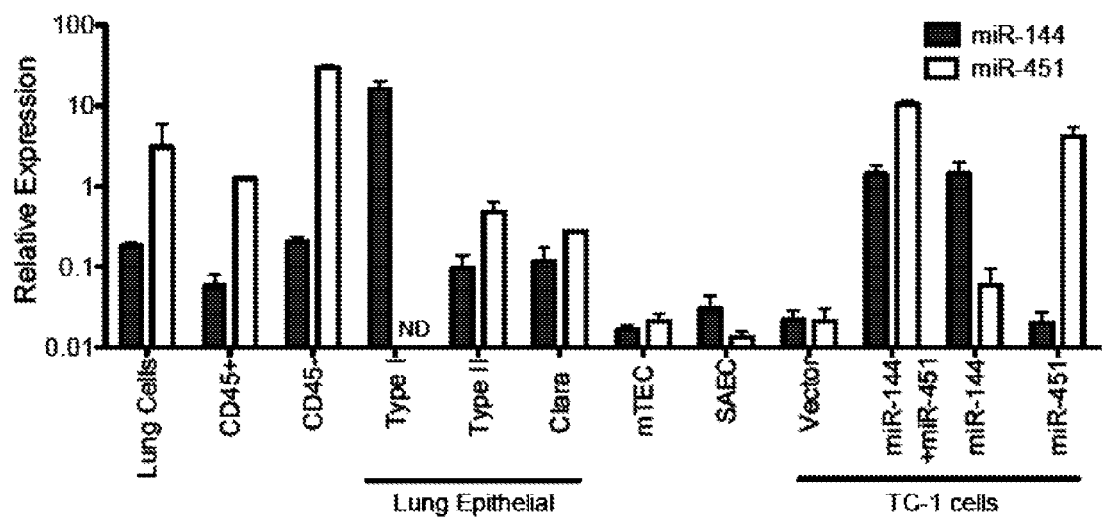

The present invention offers a convenient and expeditious way to manufacture virus for use in vaccines. The method takes advantage of the ability of cells overexpressing miR-144 to become efficient producers of virus when infected. The effect of miR-144 appears essentially independent of the type or strain of virus that is involved in the infection and can be carried out on a convenient scale. The virus grown in these cells is harvested conventionally and subsequently inactivated or "split" into vaccine components in standard procedures available in the art. Attenuated viruses may also be produced. The viral component of the vaccines can then be formulated into compositions suitable for administration to subjects. The subjects may be human or other animal subjects susceptible to the virus against which the vaccine is directed. Thus, the subjects may be any vertebrate, including mammals, fish, and birds.

The host cells in which the virus is cultured may be any cells that are susceptible to infection by the virus used. Thus, mammalian cells, insect cells, avian cells, or other animal cells may be employed. Cells currently used to produce vaccines can be modified to enhance such production as well, by modifying them to overexpress miR-144. The cells are modified to express or overexpress miR-144 or a variant thereof that retains the same activity. Suitable expression systems are readily constructed by the skilled artisan and the nature of the expression system will, of course, depend on the choice of host cell. The expression system may be designed to generate miR-144 ectopically, or the expression system may be integrated into the genome. Various vectors, including viral vectors, can be used to modify the host cells. While a variety of cells is acceptable for the method of the invention, in the case of mammalian infection, epithelial cells appear especially well adapted.

The cells modified to overexpress miR-144 are also infected with the virus the production of which is desired. As demonstrated in the examples hereinbelow, the effect of miR-144 is experienced by a wide variety of virus strains and thus this method for production is appropriate for a wide variety of virus-based vaccines. Included among such viruses are Hepatitis B and C, poliovirus, herpes virus. Both RNA and DNA viruses, and both double stranded and single stranded viruses may be produced by this method. The virus may be destined for vaccination of mammals, including humans, livestock, horses, chickens or other fowl, and the cells will be infected with the desired virus targeted to these types of subjects.

After the cells are cultured, the virus produced is recovered according to known methods and, if necessary, inactivated or "split." It is known that attenuated virus can directly be produced by modifying the virus in advance of infecting the cells. Live attenuated influenza vaccine (LAIV) has been produced by others (e.g., Gelezen, W., *Expert Rev. Vaccines* (2004) 3:131-139; Rudenko, L. G., et al., *Vaccine* (2000) 19:308-318).

If the virus has not been attenuated, further steps will be required. In one approach, the virus can be inactivated, for example, by irradiation or by using toxins such as formaldehyde or β-propiolactone. Suitable means for inactivation of viruses are well known in the art.

In the alternative, the virus may be "split" which is a catch-all term for various levels of isolation and purification of viral components to be used in vaccines. Surface antigens, for example, may be isolated or other components may be used and separated using standard separation techniques such as chromatography, selective precipitation and the like. Some vaccines which provide single components may be prepared in this way, although recombinant production of single proteins may be replacing this approach.

After the inactivated or "split" virus or attenuated virus is obtained, the vaccine is formulated using standard formulation conditions which employ conventional excipients such as buffers, preservatives, adjuvants, and the like. The vaccines may be formulated for injection or for alternative means of administration such as oral administration or transmucosal or transdermal administration. Administration by inhalation is a common option.

Thus, the vaccines of the invention are prepared using conventional techniques except that the initial virus production is enhanced by employing cell cultures of recombinant host cells that have been modified to overexpress miR-144.

There are many instances wherein it is desirable to upregulate the antiviral response mounted by a host. Of course, subjects exposed to or harboring viral infection are suitable subjects. It appears particularly advantageous to do so very early in, or prior to, infection as the ability of the intervention to inhibit replication of the virus provides a sufficient handicap to the infective agent that the immune system is better able to deal with it and this enhancement may prevent or ameliorate symptoms. On the other hand, too robust a response to viral infection may lead to undesirable effects such as inflammation, which would indicate the desirability of downregulating the response system.

Similarly, there are instances wherein the immune system is beneficially strengthened, as in response to a variety of infective agents, not just viruses, but also bacteria, protozoa or fungi. On the other hand, an excessive immune response may result in undesired side effects such as inflammation, and autoimmune diseases would also be benefited by damping down the activity of the immune system.

The present invention offers a variety of ways to manipulate both the viral response system and the immune system in a beneficial and controlled manner. Such manipulation may be done in vertebrates in general, including humans and primates. Veterinary subjects are also able to benefit from the methods of the invention, and the methods of the invention may be used to manipulate model systems for disease, both chronic and infectious. Such laboratory models include mice, rats, rabbits, as well as dogs, pigs and primates. In general, any vertebrate subject, including avian subjects, fish, mammals and marsupials are suitable as subjects for the methods of the invention.

In general, enhancement of the strength of both the antiviral response system and the immune system is effected by decreasing the level or activity of miR-144. Conversely decreasing the strength of the antiviral response system or the immune system is achieved by elevating the level or activity of miR-144.

To decrease the level of miR-144, a number of options are available. Importantly, as shown in the examples below, the therapeutic target miR-144 is present at the beginning of infection and is not diminished by virtue of the infection itself. Thus, the miR-144 target is available at an advantageous time and maintains its availability even in the presence of infection. Among methods to decrease level or activity or miR-144, for example, is introduction of antisense RNA or short interfering RNA that will directly bind or reduce the stability or activity of any miR-144 in the subject. The antisense RNA or siRNA may be in the form of a modified oligomer such that the oligomer is less susceptible to hydrolysis. For example, nucleic acids having phosphoramidate or phosphothiolate linkages might be used, as well as those with modifications of the bases, as long as the complementarity activity is not destroyed. Peptide nucleic acids could also be used. In the present specification, "nucleic acid" or "oligomer" where an oligomer composed of nucleotides is referred to, includes not only native RNA and DNA, but also DNA or RNA with modifications of the linker/and/or bases. The nature of such modifications is well known in the art, and many possibilities will be evident to the practitioner. "Modified nucleic acid" or "modified oligomer" refers to nucleic acids with modified linkages and/or bases or analogs, such as peptide nucleic acids.

The antisense or siRNA may be generated by a recombinant vector wherein a sequence that can be transcribed into the desired RNA is coupled to suitable control sequences. In addition, an antisense oligomer may be supplied in the form of DNA or RNA or modified DNA or RNA as well. Recombinant vectors that may be introduced conveniently include viral vectors and naked DNA. Thus, the levels of miRNA may be decreased by supplying materials at the nucleic acid level that either simply bind the miR-144 or decrease its stability. The levels of miR-144 are apparently controlled endogenously by the transcription factor GATA-1 (Dore, L. C., et al., *Proc. Natl. Acad. Sci. USA* (2008) 105:3333-3338) and thus manipulation of the level of this factor may also be used to increase or decrease levels of miR-144.

To inhibit the activity of miR-144, any suitable binding agent can be employed. Thus, for example, antibodies or fragments thereof may be used. The term "antibodies" in this specification includes not only fragments, but any modification of the complete antibody that retains immunospecificity. Thus, for example, single-chain recombinantly produced antibodies may also be used, as well as bispecific antibodies if desired. The antibodies may be chimeric or humanized or otherwise adjusted to be suitable for the subject to which they are administered. The binding agent may also be a "mimetic" which is a small molecule mimicking immunospecificity of an antibody or may be an aptamer.

The level of miR-144 may be increased by supplying directly a modified form thereof resistant to hydrolysis. This is the counterpart of antisense, whereas rather than an oligomer complementary to the nucleotide sequence of miR-144, an oligonucleotide with the same nucleotide sequence is introduced. In addition, recombinant expression systems for production of this RNA may be employed, including those residing on viral vectors. Further, endogenous expression may be encouraged through the GATA-1 transcription factor.

As noted above, the reason for treating a subject to modulate miR-144 levels or activity is variable. An individual subject whose antiviral response system is so intense as to cause side effects would benefit from a decrease in the level of this antiviral response, and thus from an enhanced level or activity of miR-144. On the other hand, a subject whose response to viral infection is too feeble would benefit from a reduction in levels of this microRNA. Similarly, an individual whose immune system is not adequately dealing with infection would benefit from a decreased miR-144 level or activity and the opposite would be true of an individual having an autoimmune disease, such as lupus, or an overreaction to infection.

Depending on the medicament chosen, the route of administration to the subject may vary. Oligomers of nucleotides can effectively be administered iv, ip, or intranasally. Similar routes are possible for antibodies and recombinant vectors. Suitable formulations will permit alternative forms of parenteral administration of these moieties. Small molecule and some peptide molecule medicaments that impact miR-144 may be administered orally or by suppository or by transmembrane routes.

Implications of Effects on TRAF6 Expression

Figure 10:
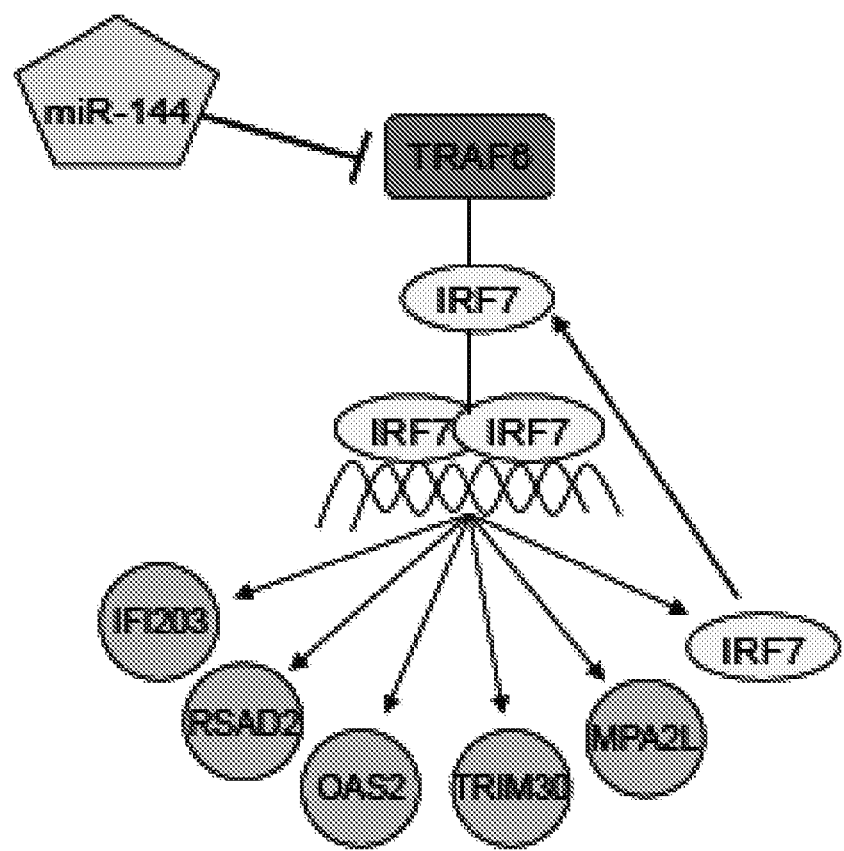
FIG. 10 shows the known complex interactions between TRAF6 and IRF7 as well as other components of the antiviral response.

As background for the methods of the invention, the implications of the ability of miR-144 to impact TRAF6 and therefore both the antiviral response system and the immune system is shown by the sequelae of TRAF6 expression illustrated in FIG. 10, which shows the known complex interactions between TRAF6 and IRF7 as well as other components of the antiviral response.

In more detail, TRAF6 is an E3 ubiquitin ligase that is critical for type I interferon responses to viral infection (Yoshida, R., et al., *J. Biol. Chem.* (2008) 283:36211). This protein positively regulates IRF7 by K63-linked ubiquitination, thereby permitting the transcriptional activity of IRF7 following its phosphorylation by various kinases (Kawai, T., et al., *Nat. Immunol.* (2004) 5:1061 and Konno, H., et al., *PLoS One* (2009) 4:e5674). This crucial interaction between TRAF6 and IRF7 is supported by the observation that when IRF7 is mutated so that it cannot be ubiquitinated by TRAF6, it fails to mediate transcriptional responses.

As TRAF6-dependent K63-ubiquitination of IRF7 is necessary for IRF7 transcriptional activity, it is possible that miR-144 modulates the expression of a network of IRF7-regulated genes by targeting the 3'-UTR of TRAF6 mRNA. Cells expressing miR-144 or siRNAs or other inhibitors of expression specific for TRAF6 should both have a similarly impaired antiviral capacity since reduced steady state TRAF6 levels are mechanistically linked to impaired IRF7-dependent transcription.

The importance of appropriately regulating the IRF7-type I interferon pathway is highlighted by the observation that dysregulated production of type I interferons underlies many chronic inflammatory and autoimmune conditions such as systemic lupus erythromatosis, cardiovascular disease, and type I diabetes (Heinig, M., et al., *Nature* (2010) 467:460, Bennett, L., et al., *J Exp Med.* (2003) 197:711-723).

Applicants provide the first demonstration that a host miRNA can negatively regulate host antiviral responses in vivo, as well as inactivate the immune response in general as shown in the examples below.

Applicants hypothesized a central role for IRF7 in the regulation of the miR-144 transcriptional network because IRF7 was the only transcription factor that was differentially expressed in response to miR-144 levels and computational predictions identified IRF7 motifs within the cis-regulatory elements of the majority of miR-144-regulated genes. It has been demonstrated previously that IRF7 is a crucial transcriptional activator of interferon-alpha (Honda, K., et al., *Nature* (2005) 434:772; Sato, M., et al., *Immunity* (2000) 13:539; and Marie, I., et al., *EMBO J.* (1998) 17:6660). In addition, IRF7 is capable of orchestrating a more extensive antiviral program through two mechanisms: 1) IRF7-dependent IFN-alpha signals in an autocrine and paracrine manner to activate the expression of genes that increase a cell's antiviral capacity, including positive feedback on the transcription of IRF7 itself, and 2) IRF7 forms transcriptional complexes with other proteins, such as IRF3, to enhance and sustain expression of this program.

To identify which of the miR-144-regulated genes are controlled both directly and indirectly by IRF7 applicants compared gene expression in the lungs of influenza-infected IRF7-null and wild type mice. As expected, it was observed that the absence of IRF7 significantly reduced the expression of type I and III interferons (Ifnα2, Ifnα4, Ifnα4, Ifnλ3, Ifnβ1) and genes with predicted antiviral functions (Oas2, Ifi203, Mpa21, Trim30, Rsad2). We did not observe differential expression of TRAF6 or IRF3 in the absence of IRF7, consistent with the lack of predicted IRF7 binding motifs in their promoters and the lack of regulation by type I interferons. These data suggest that IRF7 is necessary for normal expression of the network of genes that is perturbed by miR-144.

As used herein, "a" or "an", etc., are used to denote one or more than one of the referent unless otherwise explicitly set forth.

The following examples are offered to illustrate but not to limit the invention.

EXAMPLES

Methods

Flow Cytometry and Immunofluorescence.

Lungs were perfused with PBS and red blood cells lysed using ACK lysis buffer to ensure that miR-144 and miR-451 expression by red blood cells did not contribute to the quantification of miRNA expression within cell populations. Lungs were digested with dispase and cells were separated using CD45+ microbeads and autoMACS® separation or sorting using a FACSAria™. Live (7AAD⁻) cells were sorted as follows: CD45⁺Sca-1⁺/⁻ (hematopoietic and bronchoalveolar stem cell), CD45⁻Sca1⁻T1α⁺ (type I epithelial), CD45⁻T1α⁻Sca1⁻FITC (autofluorescence)⁺ (type II epithelial), CD45⁻Sca1⁻T1α FITC⁻ (contains Clara cells). The purity of Type II and Clara cell populations were confirmed by intracellular staining for Pro-SPC (Millipore) or Mucin (NeoMarkers), respectively. Antibodies were obtained from e-Biosciences (T1α) or BD. Formalin-fixed cells were permeabilized using 0.2% saponin, stained with anti-influenza NP (ViroStat) or anti-H1N1 (Argene) antisera followed by fluorescently-conjugated secondary antibodies, and fluorescence measured using a FACSCalibur™. Immunofluorescence was performed on cells fixed with 4% paraformaldehyde and stained for IRF7 localization using IRF7-specific antibody (H246, Santa Cruz) in PBS+BSA+0.1% saponin. Cells were imaged using a DeltaVision™ microscope and a maximum projection of 12 optical sections was prepared using ImageJ software.

Molecular Biology.

RNA was isolated using TRIzol®, cDNA was synthesized from DNase-treated RNA using random primers or miR-specific primers, and analyzed by quantitative RT-PCR using gene- or miRNA-specific primers and probes (ABI) or 384-well microfluidic miRNA arrays (ABI). Expression was normalized to EF-1 or sno202. Western blots were performed on cell lysates by serially incubating membranes with TRAF6 (sc7221, Santa Cruz), IRF7 (ab24113, Abcam), phospho-NF-κβ p65 (Cell Signaling), I-κβ (Cell Signaling), or β-actin-HRP (ab20271, Abcam) antibodies, anti-rabbit-HRP secondary antibody, and enhanced chemiluminescent detection. Nuclear extracts were prepared by hypotonic lysis and blots sequentially probed with IRF7 or nuclear lamin B1 antisera (Zymed) as a loading control. Constructs expressing both murine miR-144 and miR-451 were cloned with 145 bp upstream of pre-miR-144 and 330 bp downstream from the end of pre-miR-451. miR-451 alone was expressed with flanking sequences 100 bp upstream and 198 bp downstream. miR-144 was cloned with 145 bp upstream of pre-miR-144 and 198 bp downstream of the end of pre-miR-451; the activity of miR-451 included in this construct was ablated using site-directed mutagenesis of 7 bp of the mature miR-451. These sequences were cloned into retroviral MSCV-GFP or lentiviral pLenti6 (±GFP) vectors. Packaged virus was transduced into the indicated cells, and stably selected using 4 μg/mL puromycin (TC-1) or 2 μg/mL puromycin (SAEC cells). Influenza replication phenotypes were confirmed in cells generated by at least 3 independent transductions and transfection. Mouse IRF7, IRF1, or pEF6 plasmids were transfected into TC-1 cells (TransIT®, Mirus) and stable lines selected using 8 μg/mL blasticidin. SAECs were transduced with TRAF6 shRNA lentivirus (sc-36718V, Santa Cruz) or control scrambled shRNA lentivirus (sc-108080V, Santa Cruz) and stably selected using puromycin. Luciferase constructs were generated by cloning murine IRF7 (NM_016850, 1-1830 nt) or TRAF6 3'-UTR (BC060705, 1966-5368 nt; Open Biosystems) 3' of firefly luciferase. Wild type and mutant miR-144 target sequences in the TRAF6 3'-UTR were generated by annealing complementary 45-mer oligos containing the sequences shown in FIG. 3b flanked by restriction sites. 293T cells were transfected with pLenti6-miRNA constructs or empty vector along with the UTR-luciferase vector, which gave equivalent results to transfections performed in TC-1 cells. Cell lysates were collected after 2 d and luciferase luminescence was normalized against a Renilla luciferase control present on the same plasmid (Stop and Glo, Promega).

Mice, Cells and Viruses.

TC-1 C57BL/6 mouse lung epithelial cells, 293T, Vero cells (ATCC), and human primary bronchial or small airway epithelial cells (NHBE and SAEC, Lonza) were used where indicated. Lung cells were isolated from C57BL/6 mice using dispase, cultured to yield type I epithelial cells (SAEC) transdifferentiated from type II epithelial cells, then immortalized by transduction with MSCV-SV40 large T antigen and used after a minimal number of passages. Influenza strains (A/Puerto Rico/8/34, A/California/04/2009, A/Brisbane/59/2007, A/Udorn/1972, A/X-31) were provided by P. Thomas (St.

Jude's, Memphis, Tenn.), A/Udorn/1972 was provided by R. Krug (University of Texas, Austin, Tex.) and A. Bergthaler (Institute for Systems Biology, Seattle, Wash.) and vesicular stomatitis virus (VSV) and encephalomyocarditis virus (EMCV) (ATCC) were provided by J. Rajan (Institute for Systems Biology, Seattle, Wash.).

Viral Infection.

Cells were infected with influenza at a multiplicity of infection (MOI) of 5 for 1 h in Opti-MEM® in the absence of trypsin, the inoculum removed by washing, and cells cultured in Opti-MEM® for 18-24 h. RNA was collected at 1 h using TRIzol® to quantify initial viral load and RNA, protein, and cell supernatants were collected after 18-24 h. Where indicated, type I interferons were blocked using neutralizing antibodies (RMMA-1 and RMMA-2, PBL) Viral RNA was quantified by RT-PCR using primers specific for influenza M gene (Forward 5' CAT GGA ATG GCT AAA GAC AAG ACC (SEQ ID NO:1), Reverse 5' CCA TTA AGG GCA TTT TGG ACA (SEQ ID NO:2), Probe FAM-5' TTT GTG TTC ACG CTC ACC GTG CCC A-TAMRA (SEQ ID NO:3)) and normalized to the level of mouse EF-1a or human GAPDH or RNA obtained from equivalent volumes of supernatants. To permit comparison between experiments, viral load at 24 h was normalized to initial viral load at 1 h where indicated. Influenza plaque assays were performed by plating serial dilutions of 24 h cell supernatants on MDCK cells in duplicate, overlaying with agarose, and enumerating crystal violet-stained plaques. Cells were infected with EMCV (MOI=0.01) and VSV (MOI=0.01) in complete DMEM for 1 h, cells washed, and incubated for 24 h. EMCV and VSV plaque assays were similarly performed using Vero cells and methyl cellulose overlay. C57BL/6 wild type, IRF7-null, miR-144/miR-451−/− (backcrossed to C57BL/6) or +/+ littermate mice were challenged with $10^5$ pfu influenza PR8 in 30 µl intranasally and lung RNA isolated using TRIzol® after 12 h or 24 h.

Computational Analysis.

RNA was isolated from TC-1 cells expressing either MSCV empty vector or MSCV-miR-144+451 and both infected with influenza PR8 for 24 h. Labeled RNA was hybridized to Affymetrix® mouse exon arrays (1.0), RMA normalized, and differential expression analysis was performed using the bioconductor package Limma. Genes with a p value threshold of <0.05 and fold change >2 were retained for further analysis. Promoter sequence (1 kB) were scanned for transcription factor motifs (TRANSFAC 7.0) using FIMO (MEME suite) 12 with a p value cut-off of 0.0001. GOMiner was used for GO enrichment determination and miRWalk was used for miR-144 target prediction, with miRWalk, TargetScan, and RNA22 predicting the miR-144 target sequence in TRAF6. Network visualization was performed using Cytoscape (located on the World Wide Web at cytoscape.org).

Statistical Analysis.

Significance was determined using an unpaired 2-tailed Student's t test.

Example 1 miR-144 Impairs Host Control of Viral Replication

A systems biology approach was used to profile microRNAs in influenza-infected lung. High expression of both miR-451 and miR-144 was found in mouse lung. Since these microRNAs have not previously been characterized within the lung, we used a cell sorting strategy to identify which cell lineage(s) express miR-144 and miR-451. When cells were separated on the basis of CD45 expression (a marker for hematopoietic cells) and markers of epithelial cells, we observed the highest expression of miR-144 in type I lung epithelial cells and high miR-451 expression in a broader range of hematopoietic and epithelial cell lineages.

Expression of miR-144 and miR-451 in isolated FACS-sorted mouse lung cell populations: Expression in primary polarized tracheal epithelial cells (mTEC), cultured primary type I lung epithelial cells (SAEC), and mouse TC-1 epithelial cell lines with or without stable transduction of microRNAs was measured by quantitative RT-PCR and plotted in arbitrary units relative to sno-202 expression. Means+/−SEM are shown for 4-8 samples in FIG. 1A. ND indicates not detected. Expression is equivalent to the level measured in infected cells and lungs (data not shown).

Figure 1B:
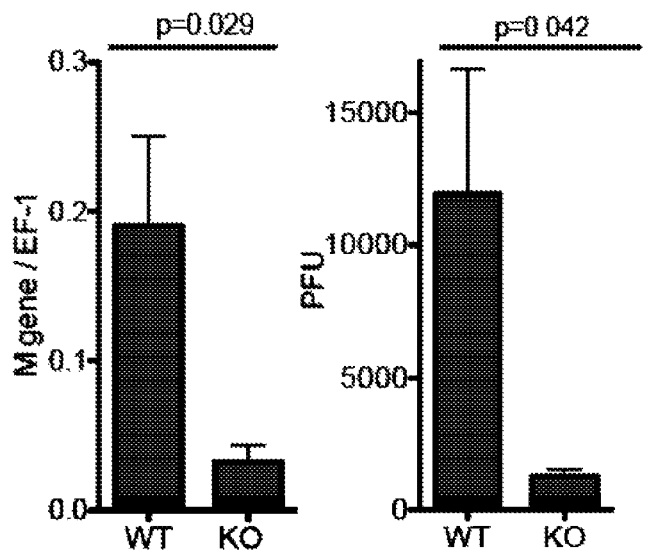

The expression of miR-144 and miR-451 within the natural host cells for influenza replication suggested a possible role beyond their characterized function in the erythroid compartment. We therefore tested the effects of these microRNAs on influenza infection in vivo. We infected miR-144/miR-451 null mice with influenza PR8 and measured a 6-fold decrease in lung viral load and a 9-fold decrease in infectious virus isolated by lung lavage after 12 hours, indicating that miR-144 and/or miR-451 regulate host cell antiviral responses. See FIG. 1B.

Lung viral load was quantified by qRT-PCR of viral M gene and normalized to host EF-1 in miR-144/miR-451−/− (KO) or wild type (WT) mice following intranasal infection with influenza for 12 hours. Viral load in lung lavage fluid was quantified by plaque assay. Means±SEM are shown for 8 mice per group in two independent experiments in FIG. 1B.

Obtaining a mechanistic understanding of this in vivo phenotype required relevant in vitro models that would permit experimental modulation of miRNA expression. We measured miR-144 and miR-451 expression within three tractable cell culture models: primary polarized tracheal epithelial cells (TEC), primary small airway type I epithelial cells (SAEC), and the TC-1 lung epithelial cell line. When these cells were infected with influenza A or stimulated with type I interferon in vitro, we observed constitutive miRNA expression that was not modulated by these viral agonists (data not shown).

SAEC and TC-1 cells were chosen for subsequent studies for the following reasons: stable cell lines over-expressing miRNAs could be generated, low basal expression of miR-144 and miR-451 permitted gain-of-function studies, and these cells permitted influenza infection and replication.

Figure 1C:
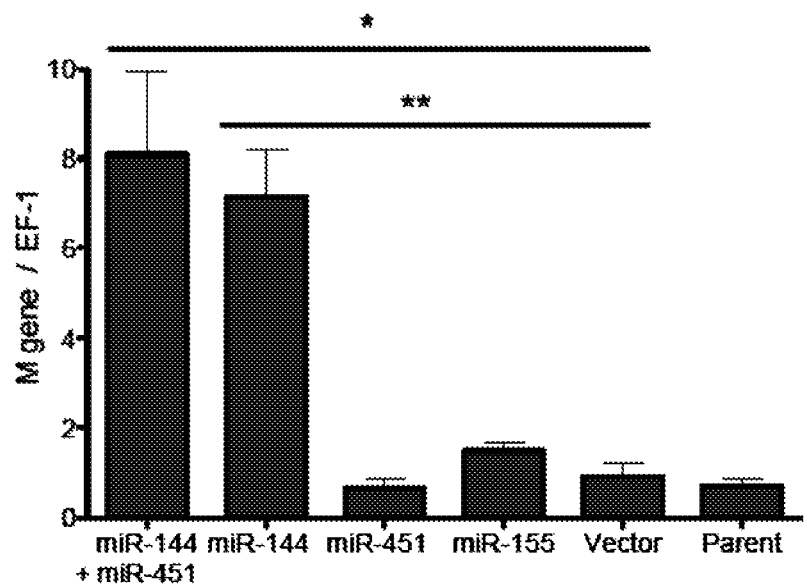

We generated lines of TC-1 mouse lung epithelial cells stably over-expressing miR-144, miR-451, or vector alone and infected these cells with influenza PR8. Ectopic expression of miR-144 significantly increased the load of viral genomes as measured by M gene (FIG. 1C). This phenotype was also observed in immortalized murine primary small airway type I epithelial cells (SAEC) using quantitative RT-PCR for viral genomes.

In order to confirm that the impaired antiviral phenotype was not a non-specific response generated by expressing microRNAs in general, we observed that two unrelated microRNAs (miR-451 and miR-155) did not increase viral load (FIG. 1C). As shown, TC-1 cells were transduced with retrovirus expressing GFP and miR-451+miR-144, miR-144, miR-451, miR-155, or retroviral vector alone and stable lines were generated using puromycin selection and compared with untransduced (parent) cells. Cells were infected with influenza PR8 and viral load at 24 hours was quantified by qRT-PCR of viral M gene and normalized to host EF-1.

Means±SEM for 3-7 independent experiments are shown and p values calculated relative to vector control cells, as seen in FIG. 1C.

Figure 1D:
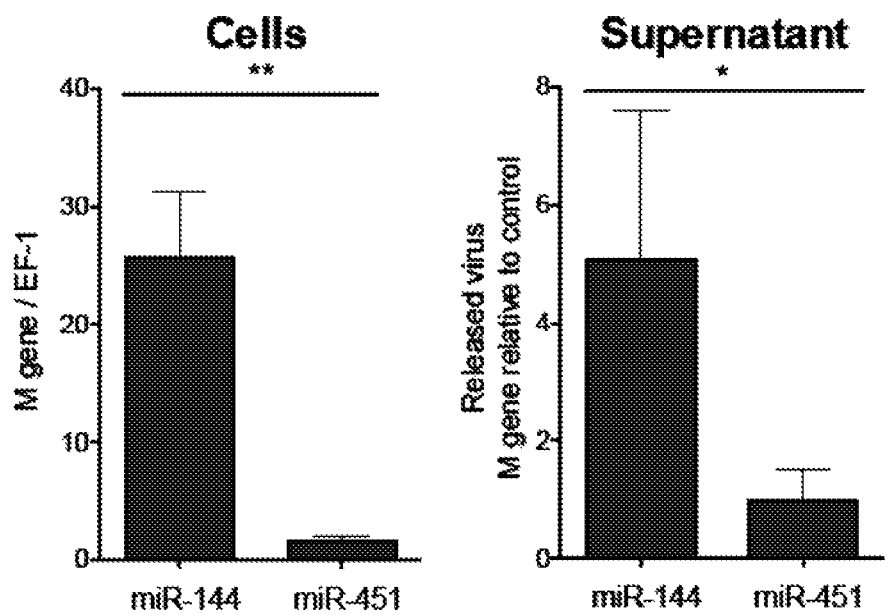

Primary mouse small airway epithelial cells (SAEC) were immortalized while being transduced with retrovirus expressing miR-144 or miR-451. Cells were infected for 18 hours and M gene measured as described above, and means±SEM are shown (n=6) and results confirmed in 5 independent experiments. Virus released from cells was quantified as shown in FIG. 1D by measuring M gene in the cell supernatants of miR-144-expressing cells relative to miR-451-expressing cells (n=7).

Figure 1E:
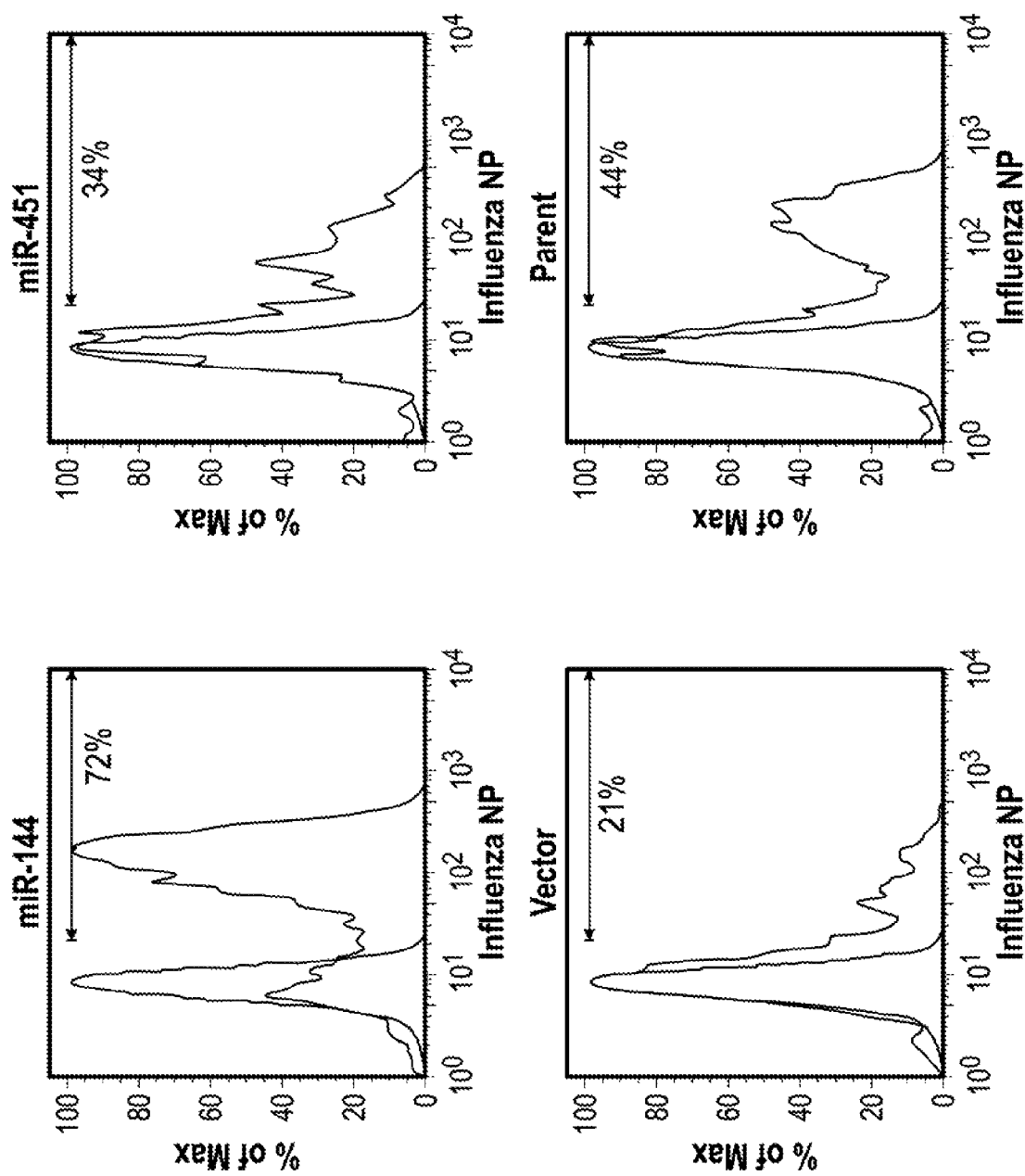

SAECs were infected as described and the percentage of influenza NP positive cells quantified by flow cytometry as in FIG. 1E. The unfilled dotted line represents data from stained uninfected cells. Data are representative of 5 independent experiments. Forward scatter (FSC).

Figure 1F:
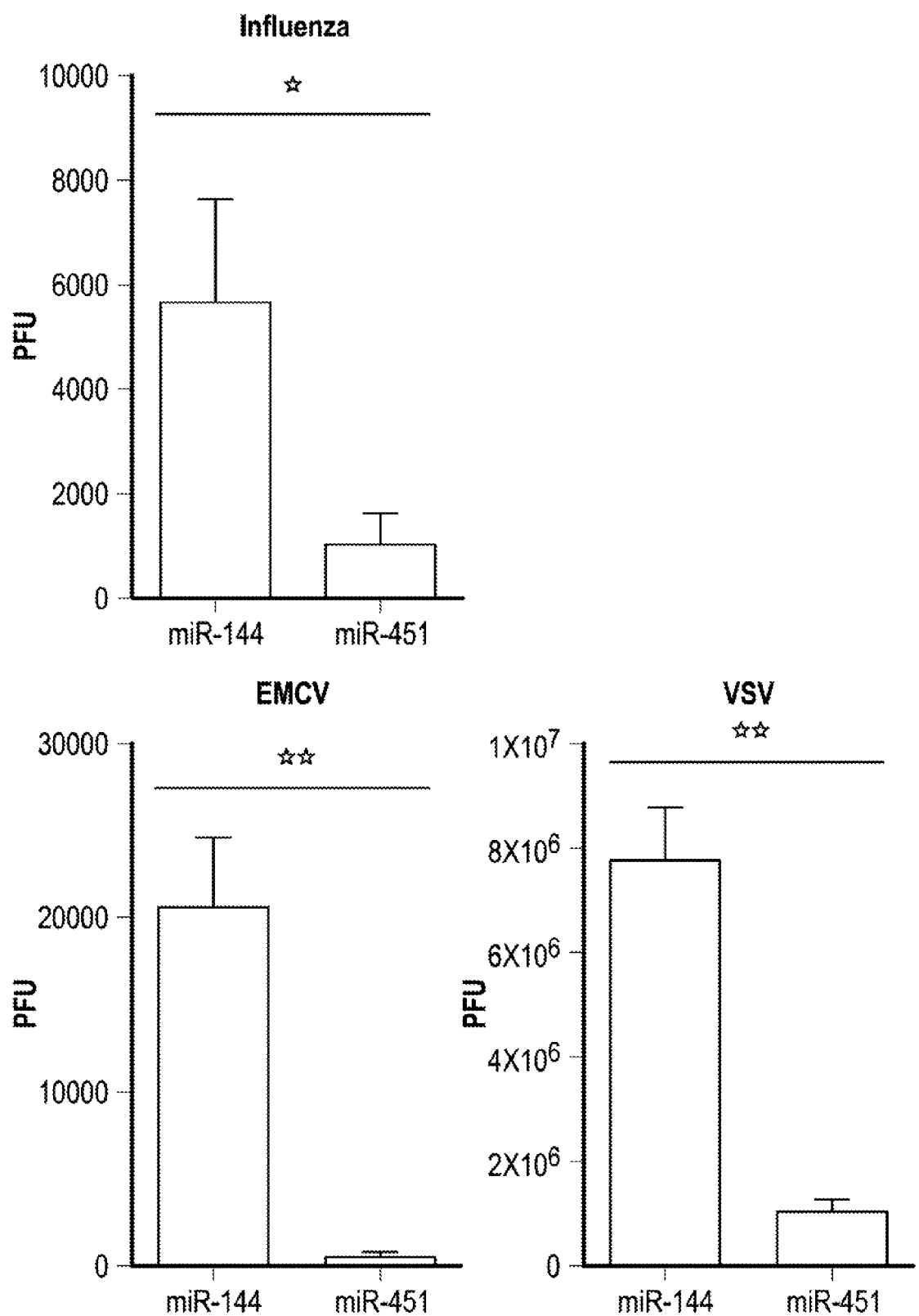

FIG. 1F shows that miR-144 expression increased titers of two negative-sense ssRNA viruses, influenza (10-fold) and vesicular stomatitis virus (VSV, 7-fold), as well as a positive-sense ssRNA virus, encephalomyocarditis virus (EMCV, 50-fold), indicating that the effect of miR-144 is not unique to influenza infection Immortalized SAECs were infected with influenza, EMCV, or VSV and plaque assays performed on supernatants collected 24 hours post-infection as shown in FIG. 1F. Means±SEM are shown for 6-10 biological replicates in 3 independent experiments. * p<0.05 ** p<0.01.

Figure 2A:
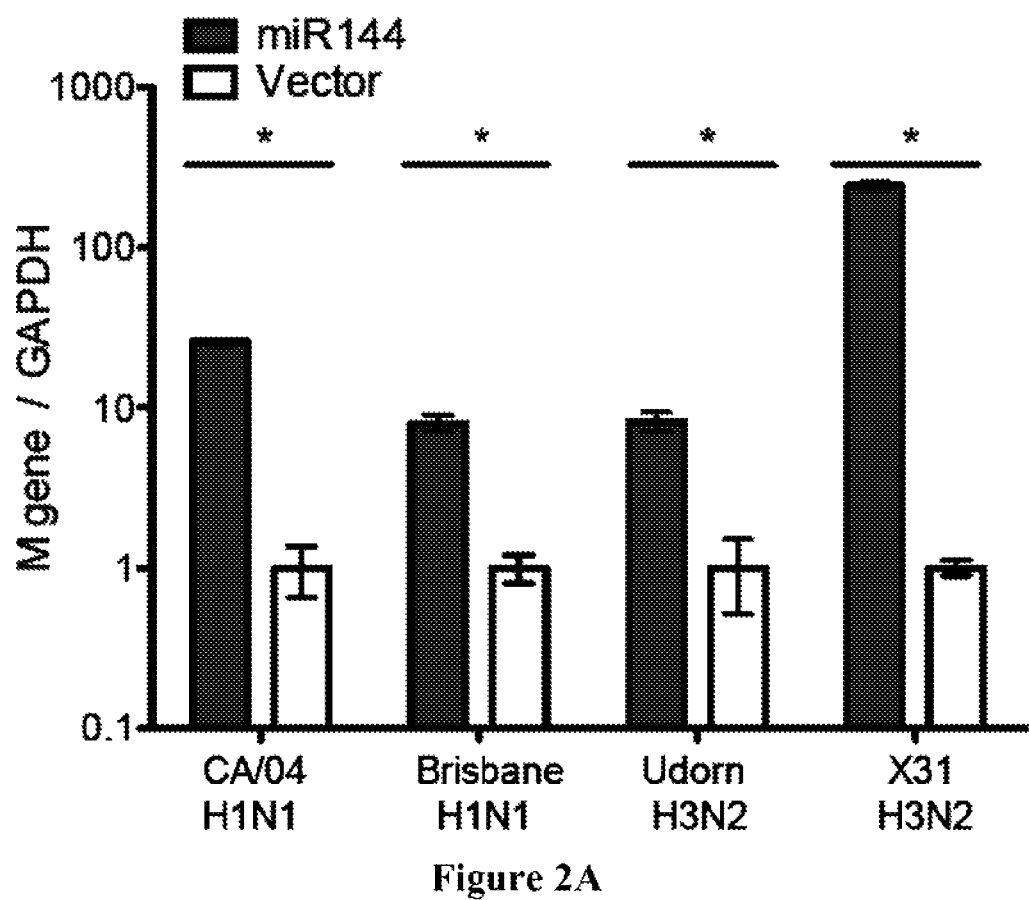
Figure 2B:
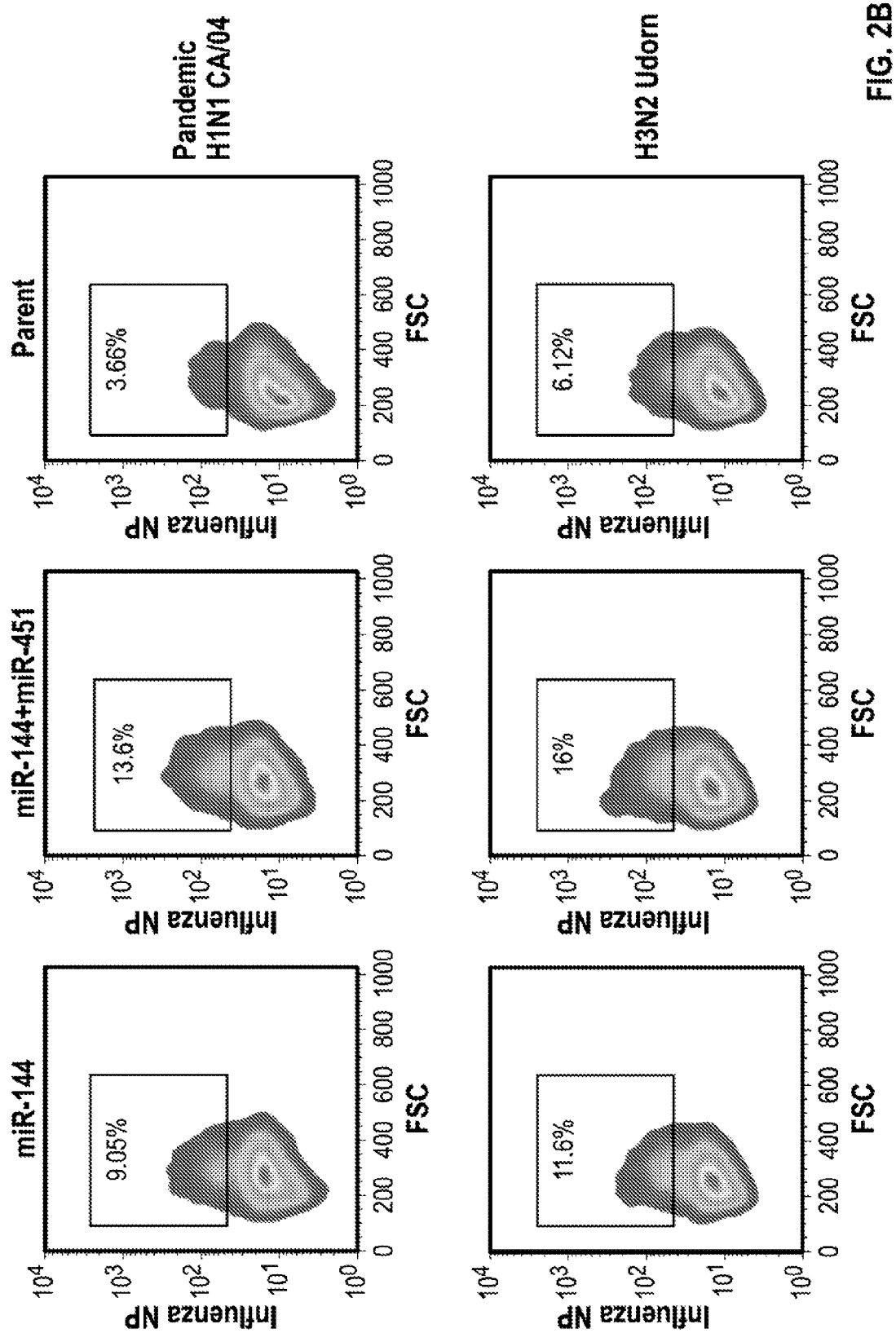

The results shown in FIGS. 1A-1F represent results in murine cells. FIGS. 2A and 2B reflect corresponding results in human cells.

To determine whether miR-144 expression similarly increased the viral load of clinical isolates, we generated primary normal human bronchial epithelial cells expressing various miRNAs and found that miR-144 significantly increased viral loads of swine-origin pandemic and seasonal H1N1 influenza viruses (CA/04 and Brisbane) as well as laboratory-adapted H3N2 strains (X-31 and Udom) as determined by quantification of viral genomes and NP protein. Concordant results were obtained using primary human small airway epithelial cells.

Human primary bronchial epithelial cells were transduced with lentiviral constructs encoding miR-144 or vector alone. Cells were infected with the indicated strains of influenza and viral load at 24 hours was quantified by qRT-PCR of viral M gene and normalized to host GAPDH. Means±SEM for triplicate samples are shown in FIG. 2A and representative of 3 independent experiments. p values were calculated relative to vector alone control cells. * p<0.01.

Primary human bronchial epithelial cells were transduced with lentiviral constructs encoding miR-144 or vector alone. Cells were infected with the indicated strains of influenza and stained for viral N protein with labeled antibody. Data in FIG. 2B are representative of 3 independent experiments. In FIG. 2B, the cells stained with antibody appear in the boxed portion of the results where the percentage of cells expressing N protein is clearly higher in the cells transduced to express miR-144 as compared to the parent.

Example 2 miR-144 Regulates the IRF7 Transcriptional Network

Figure 3A:
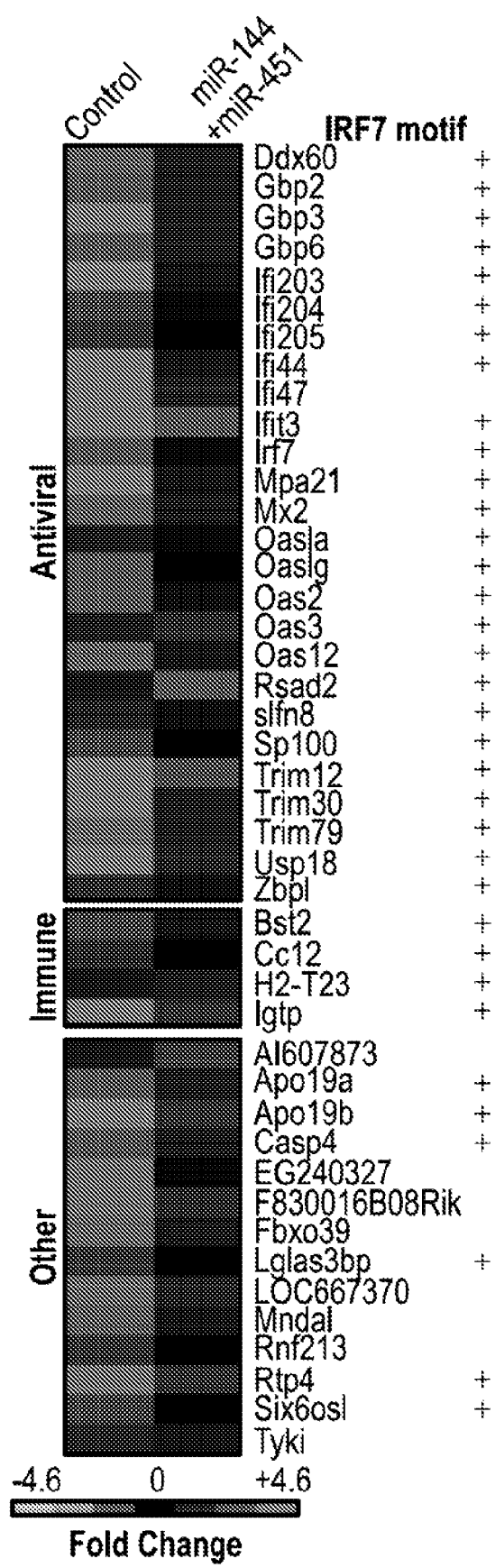

To elucidate the mechanism whereby miR-144 increases influenza replication within lung epithelial cells, TC-1 cells stably over-expressing miR-144 were infected with influenza A for 24 hours and the transcriptional profile was compared with that of infected control cells. Expression of miR-144 significantly decreased the expression of 44 genes and increased the expression of 5 genes (FIG. 3A and data not shown). A predominant feature of the array data was the suppressed expression of genes associated with antiviral and interferon responses by miR-144, as shown in the heat map in FIG. 3A (cluster 1; enriched gene ontology (GO) functional categories: defense response to virus and immune response (p<0.05)). This suppression was also observed prior to infection (data not shown).

Transcriptional analysis was performed using microarrays. Genes whose expression change following influenza infection differed by more than 2-fold (p<0.05) between cells expression miR-144 and cells expressing vector alone were clustered by biological function and represented in a heat map with red representing upregulation following infection and green representing downregulation. Mean intensities for 3 independent experiments are shown relative to uninfected control (vector alone) cells. Genes containing IRF7 motifs within 1 kB of the transcriptional start site are indicated by + in FIG. 3A.

Figure 3B:
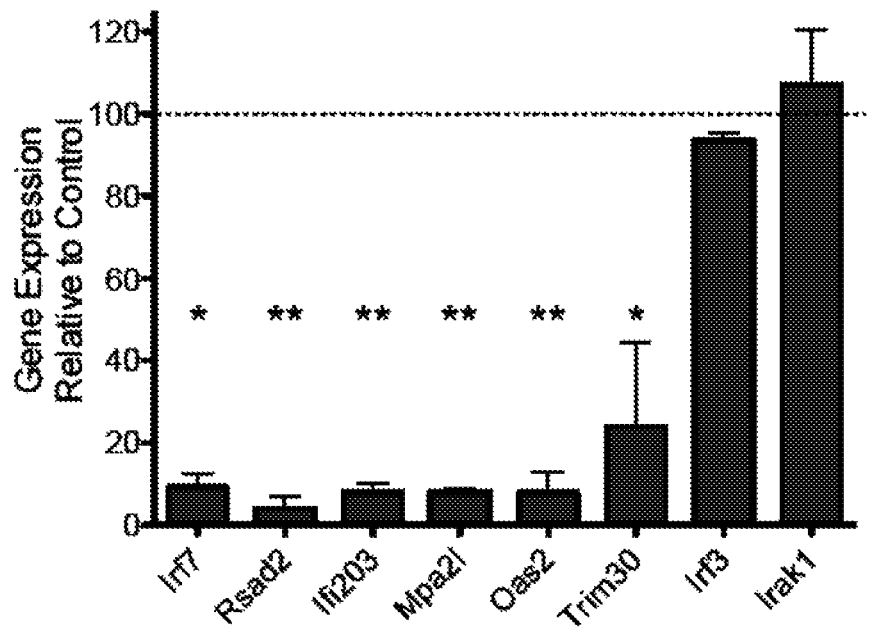

We validated the differential expression of several characterized and putative antiviral effectors (Rsad2, Ifi203, Mpa21, Oas2, and Trim30) and the transcription factor IRF7 by quantitative RT-PCR in cells transduced to express miR-144 (FIG. 3B). In contrast, miR-144 expression did not decrease steady state levels of IRF3 or Irak1, showing specificity in the regulation of a unique subset of antiviral genes by miR-144 (FIG. 3B). RNA was isolated from cells infected for 24 hours and the expression level in miR-expressing cells is shown as a percentage of the level in vector-only control cells. Means and SEM for 3 independent experiments are shown in FIG. 3B.

Figure 3C:
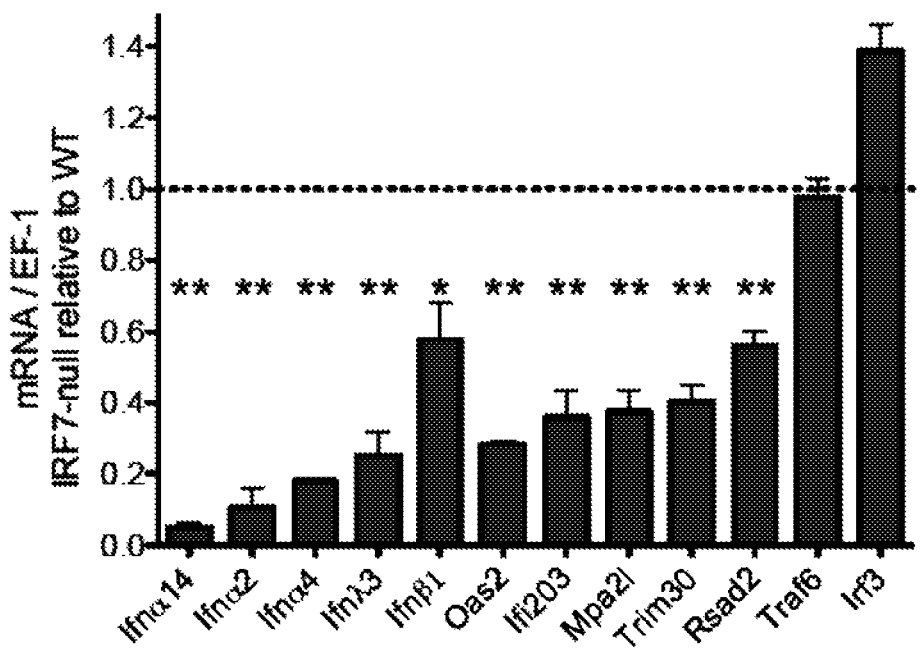

The effect of IRF7 on gene expression was also tested in vivo. WT or IRF7$^{-/-}$ mice were infected with $10^5$ pfu influenza PR8 and lungs harvested after 24 hours. Gene expression was normalized to EF-1. Means±SEM of IRF7$^{-/-}$ relative to wild type mice are shown with n=3 mice per genotype in FIG. 3C. The absence of IRF7 significantly reduced the expression of type I and III interferons (Ifnα2, Ifnα4, Ifnα4, Ifnλ3, Ifnβ1) and genes with predicted antiviral functions (Oas2, Ifi203, Mpa21, Trim30, Rsad2). We did not observe differential expression of TRAF6 or IRF3 in the absence of IRF7, consistent with the lack of predicted IRF7 binding motifs in their promoters and the lack of regulation by type I interferons. These data suggest that IRF7 is necessary for normal expression of the network of genes that is perturbed by miR-144.

Figure 3D:
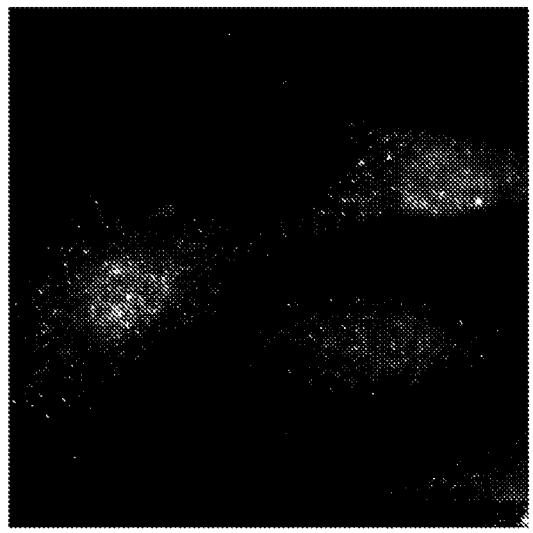
Figure 3D:
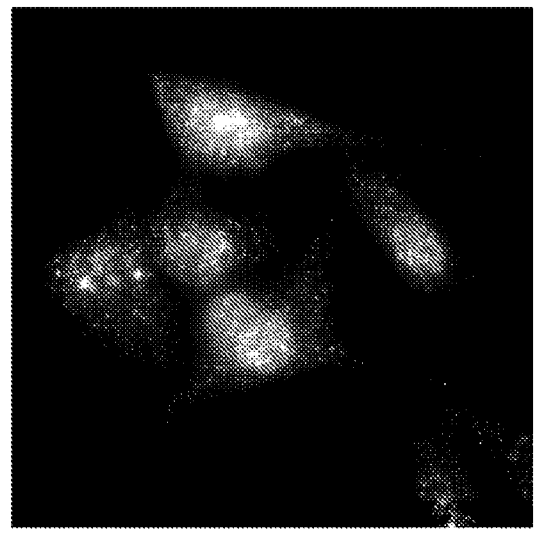

SAECs expressing either miR-144 or miR-451 were infected with influenza PR8 for 2 h. IRF7 localization was determined by immunofluorescence. Decreased nuclear localization of IRF7 was observed in miR-144-expressing cells at 6 h. Reduced nuclear translocation of IRF7 was also observed at 2 hours post-infection as shown in FIG. 3D and in uninfected cells (data not shown).

Figure 3E:
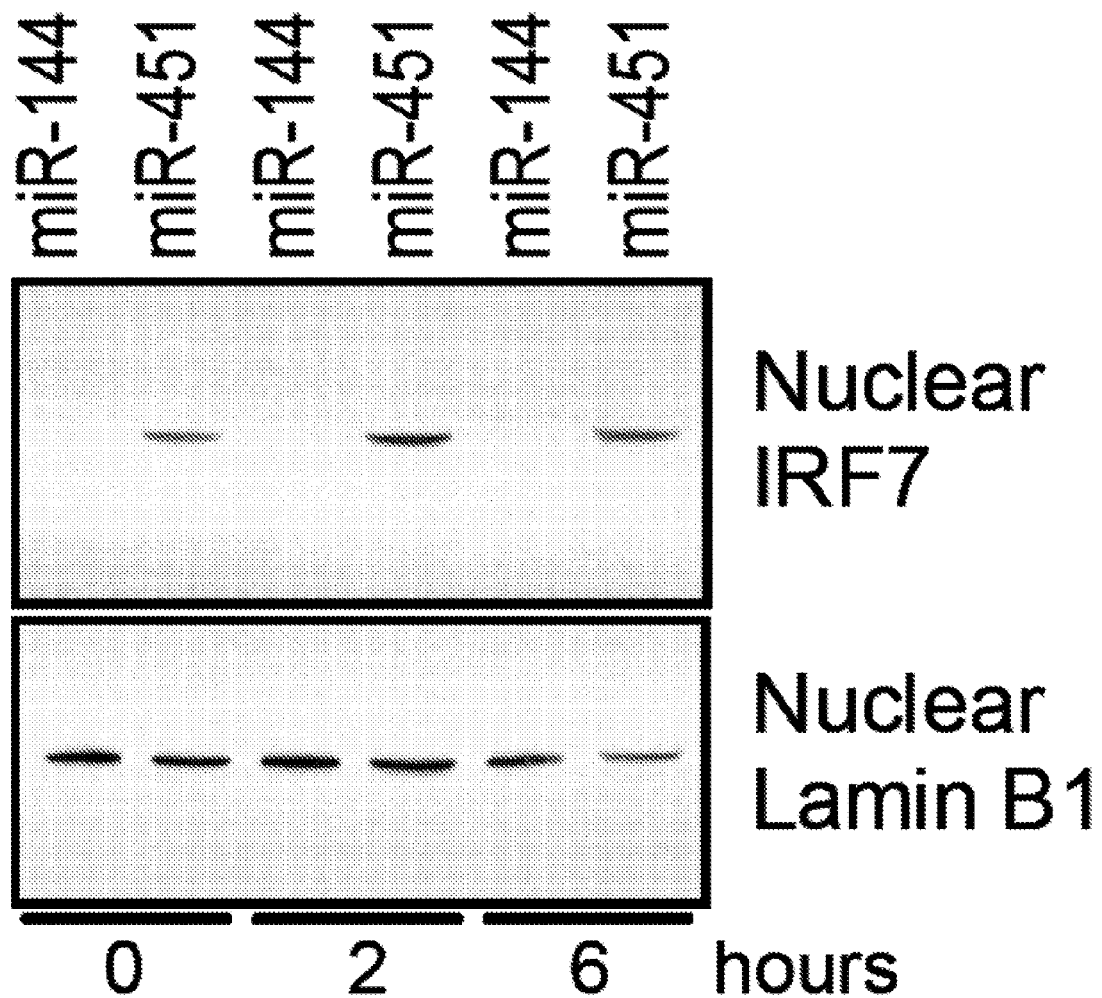

SAECs expressing either miR-144 or miR-451 were infected with influenza PR8 for 2 h or 6 h. Nuclear extracts were prepared from infected and uninfected cells and nuclear IRF7 was quantified by Western blotting and nuclear lamin B1 levels were assessed as a loading control. Data in FIG. 3E are representative of 3 independent experiments.

Figure 3F:
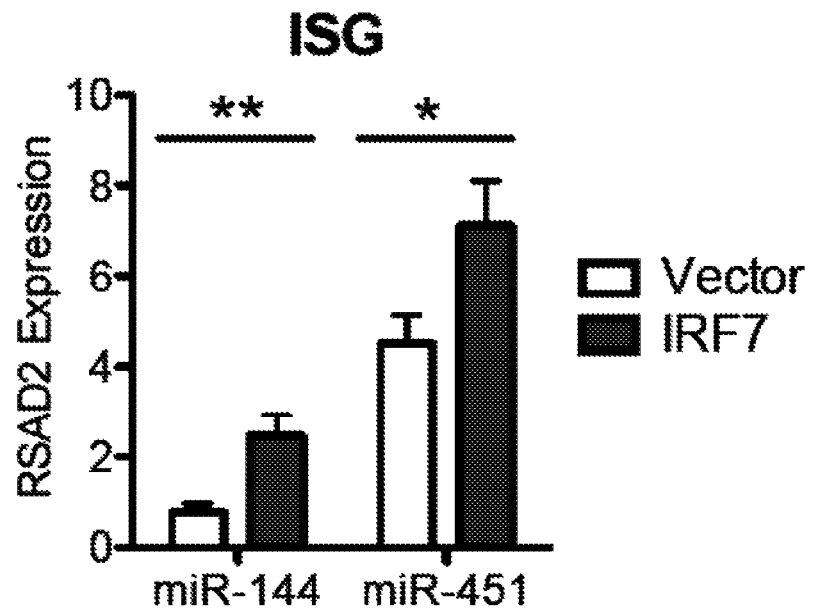

We examined whether IRF7 could functionally complement the diminished antiviral capacity of epithelial cells expressing miR-144. Stable cell lines were generated to express either miR-144 or miR-451 along with either IRF7 (lacking the 3'-UTR sequence to eliminate possible post-transcriptional regulation by miR-144) or vector alone, as described. Quantitative RT-PCR using gene-specific primers for interferon-stimulated genes (ISG) was performed following infection with influenza for 24 hours and expression normalized to levels of EF-1. Data are shown in FIG. 3F for Rsad2 and are representative of data obtained for other ISGs (Oas2, Mpa21, Ifi203, and Trim30; data not shown). Means±SEM are shown for 3 biological replicates.

Figure 3G:
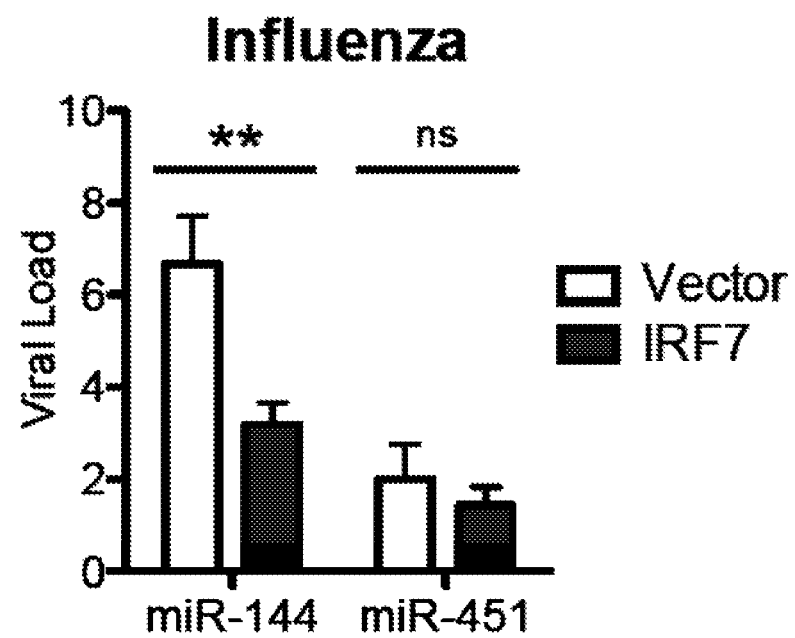

Viral load was quantified in the cells described in FIG. 3F. The mean fold increase in M gene levels normalized by EF-1 expression in cells infected for 24 hours is shown in FIG. 3G for 3 biological replicates±SEM. * p<0.05 ** p<0.01.

Thus, impaired antiviral activity of miR-144-expressing cells is restored by IRF7 expression.

Figure 3H:
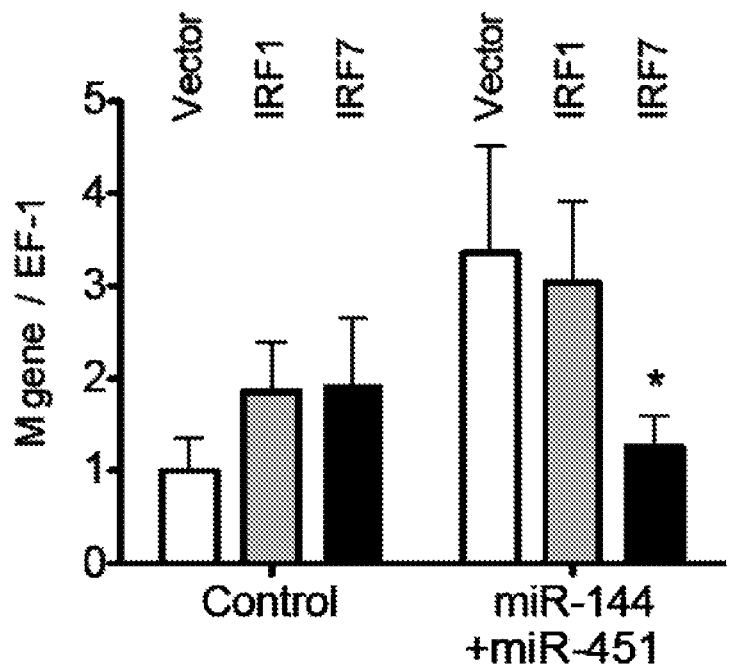

Stable lines of TC-1 cells were generated that expressed combinations of empty retroviral GFP vector (control) or GFP-+miR-144+miR-451, and pEF6-IRF7 (lacking the 3'-UTR sequence to eliminate possible post-transcriptional regulation by miR-144), pEF6-IRF1 (negative control) or pEF6 vector alone, as described. M gene levels in cells infected for 24 h were normalized by EF-1 and displayed relative to GFP+pEF6 cells to permit comparison between experiments. Means±SEM were calculated from 3 independent experiments are shown in FIG. 3H.

Figure 3I:
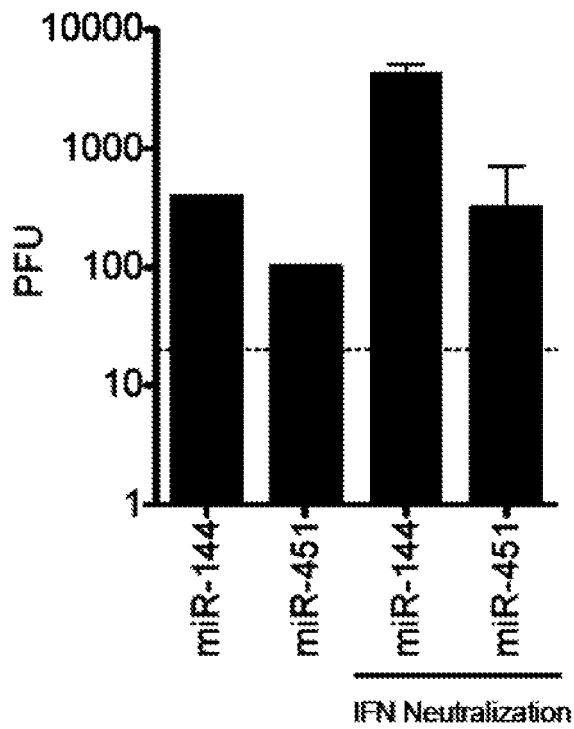

SAEC cells expressing either miR-144 or miR-451 were infected with influenza for 24 h and the indicated cells were incubated with neutralizing antibodies to IFN-alphas and IFN-beta. Released virus was quantified in the supernatants by plaque assay. Means±SEM were calculated from 2 independent experiments performed in duplicate. * p<0.05, ** p<0.01 as shown in FIG. 3I.

Ectopically expressed IRF7 restored expression of the antiviral target genes illustrated in FIG. 3B as shown in FIG. 3F and reduced the viral load in cells over-expressing miR-144 but not in control cells expressing miR-451 (FIG. 3G). In contrast, the transcription factor IRF1, which also regulates many antiviral genes but whose expression is not affected by miR-144, did not functionally complement the impaired antiviral response of miR-144 expressing cells (FIG. 3H). The proviral effect of miR-144 was observed even when type I interferons were blocked, suggesting that increased interferons resulting from ectopic IRF7 expression cannot solely explain the complementation (FIG. 3I).

Example 3 miR-144 Directly Regulates TRAF6 Expression

We functionally tested whether IRF7 mRNA is a direct target for miR-144, despite its lack of a computationally predicted miR-144 target sequence. We fused the full coding sequence of IRF7 together with the 36 nucleotide 3'-UTR to firefly luciferase and transfected constructs into 293T cells along with miR-144 or either of two negative controls (miR-451 or empty vector). Ectopic expression of miR-144 did not alter expression of this IRF7-luciferase construct (FIG. 4A); thus decreased IRF7 mRNA levels in miR-144-expressing cells do not result from a direct interaction between IRF7 and miR-144.

Figure 4C:
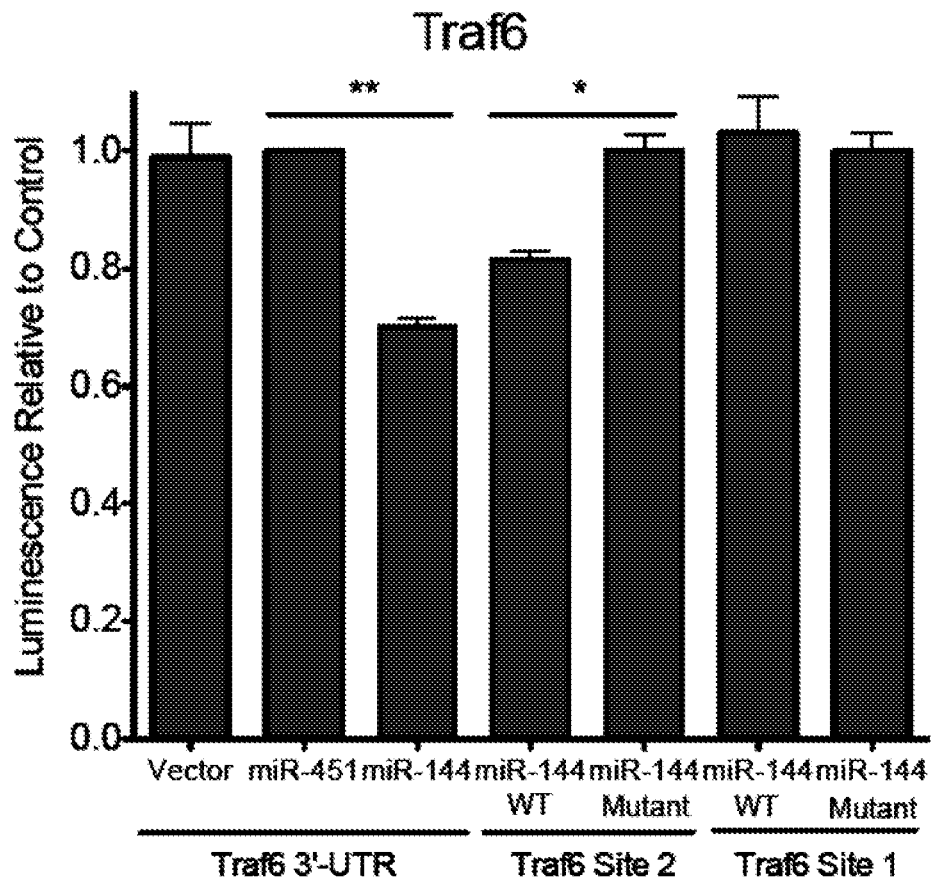

To establish how miR-144 inhibits IRF7 expression, we identified additional proteins with connectivity to the IRF7 gene regulatory network using the network visualization program Cytoscape. Computational prediction of miR-144 binding sites in the coding and non-coding sequences of the genes belonging to this expanded network yielded TRAF6 as the strongest candidate, with two predicted canonical target sequences in its 3'-UTR. We fused the complete TRAF6 3'-UTR (shown in FIG. 4B) to firefly luciferase and measured a significant decrease in luminescence only in the presence of miR-144 (not with miR-451 as a control), to an extent in concordance with published studies for other miRNA-dependent effects (FIG. 4C). This indicates that miR-144 can post-transcriptionally regulate TRAF6. As mentioned above, TRAF6 is predicted to contain 2 miR-144 target sequences in its 3'-UTR. We generated luciferase constructs containing individual intact or mutated miR-144 target sites shown in FIG. 4B. Mutation of 7 nucleotides in the predicted miR-144 target sequence in site 2 completely abrogated the negative effect of miR-144 on expression of the reporter construct, while mutating the same nucleotides in site 1 had no effect (FIG. 4C).

293T cells were transfected with two plasmids: a lentiviral construct encoding miR-144, miR-451, or vector alone, and a reporter plasmid encoding both Renilla luciferase to normalize for transfection efficiency and firefly luciferase fused to the complete coding sequence plus 3'-UTR of murine IRF7. Luminescence from firefly luciferase normalized by Renilla luminescence was graphically represented relative to cells expressing miR-451. Means±SEM for 4 independent experiments performed in triplicate are indicated. Concordant results in FIG. 4A were obtained in TC-1 lung epithelial cells.

Luciferase assays were performed using firefly luciferase fused to the complete 3'-UTR of murine TRAF6 or the intact or mutant miR-144 target sites in the TRAF6 3'-UTR shown in FIG. 4B. Cells were co-transfected with miR-144, miR-451, vector alone, or individual wild-type or mutated miR-144 target sequences in the TRAF6 3'-UTR, as indicated. Means±SEM for 5 (complete UTR) or 3 (individual miR-144 sites) independent experiments performed in triplicate are shown in FIG. 4C. *p=0.014 **p=0.010.

Western blot of TRAF6 levels in TC-1 cells expressing miR-144 or miR-451 prior to infection or 6 hours post-infection with influenza PR8. Images in FIG. 4D are representative of 4 independent experiments.

Figure 4D:
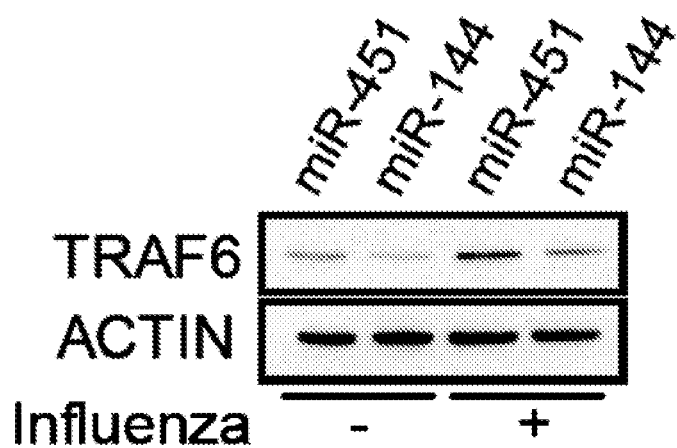

The luciferase data were further reinforced by the observation that TRAF6 protein levels were significantly reduced in cells expressing miR-144 (FIG. 4D). TRAF6 has also been shown to be regulated by miR-146a (Hou, J., et al., *J. Immunol.* (2009) 183:2150); we excluded the possibility that miR-144 regulates TRAF6 via miR-146a by determining that miR-144 expression did not alter the expression of miR-146a expression in cells or mice (data not shown).

Figure 5A:
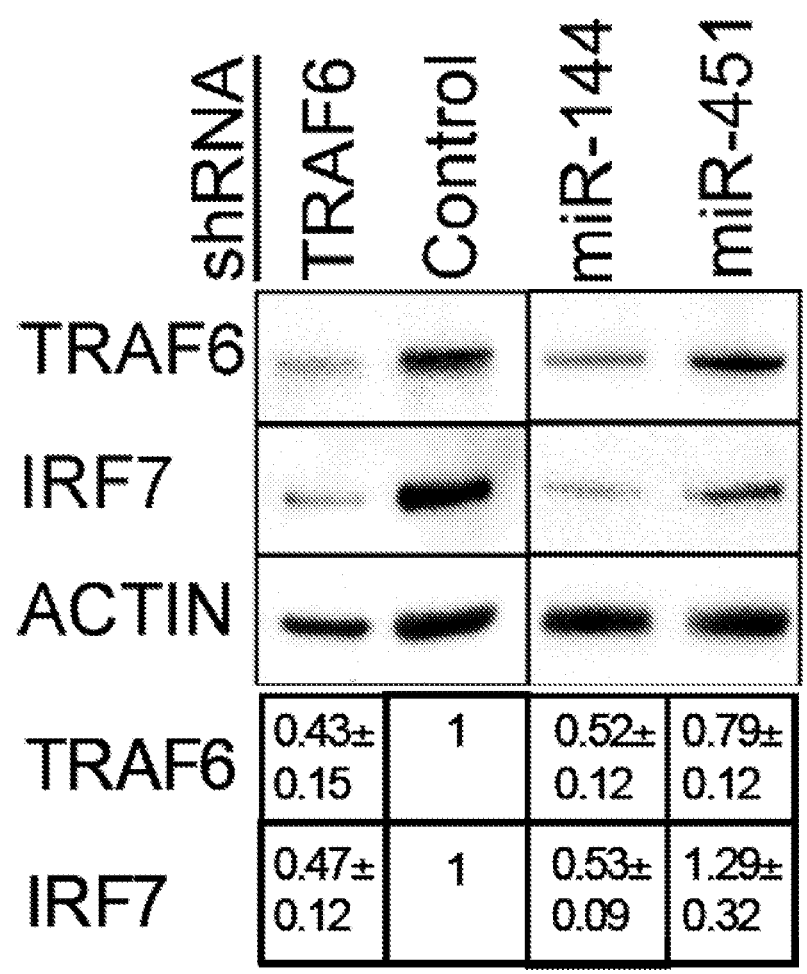

To further test this hypothesis, we generated immortalized SAECs expressing miR-144 or shRNAs specific for TRAF6, along with control cells expressing miR-451 or non-functional shRNA and determined TRAF6 protein levels by Western blot. Western blotting of TRAF6, IRF7, and β-actin was performed using protein lysates from the indicated SAEC cells. Densitometric quantification of IRF7 or TRAF6 abundance relative to actin in 3-4 experiments is shown relative to shRNA control cells in FIG. 5A. TRAF6 protein levels were reduced in cells engineered to express either TRAF6-specific shRNAs or miR-144, relative to control cells and reduced TRAF6 levels were associated with reduced IRF7 protein (FIG. 5A) and mRNA levels, which is expected as IRF7 positively feedbacks on its own transcription to amplify the IRF7-dependent transcriptional program.

Figure 5B:
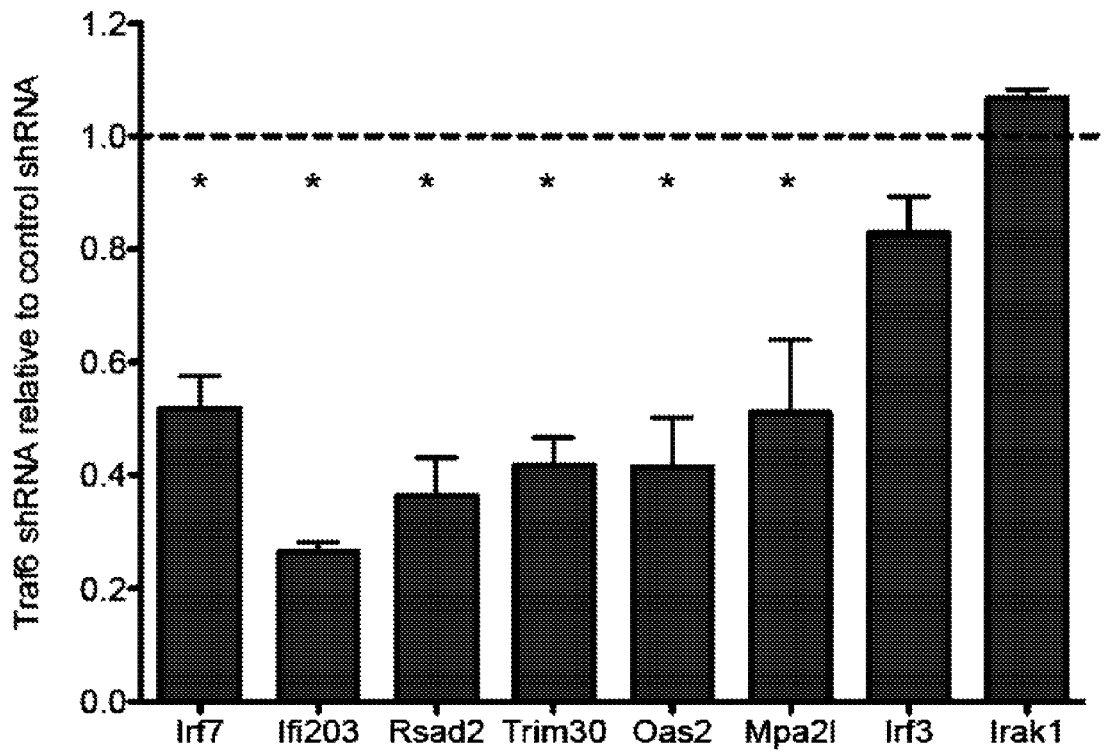

These decreased levels of IRF7 have functional consequences for the IRF7 network. For example, expression of Ifi203, Rsad2, Trim30, Oas2, and Mpa21 is impaired when TRAF6 expression is downregulated by specific shRNA (FIG. 5B) or miR-144 (FIG. 3B). Quantitative RT-PCR was performed using gene-specific primers and RNA isolated from SAECs stably-expressing TRAF6-specific or control shRNA following influenza PR8 infection for 18 hours. Gene expression in cells expressing TRAF6-shRNA was normalized by EF-1 and shown as a percentage of the level in control shRNA cells. Means±SEM for 3 independent experiments performed in duplicate are shown in FIG. 5B.

Figure 5C:
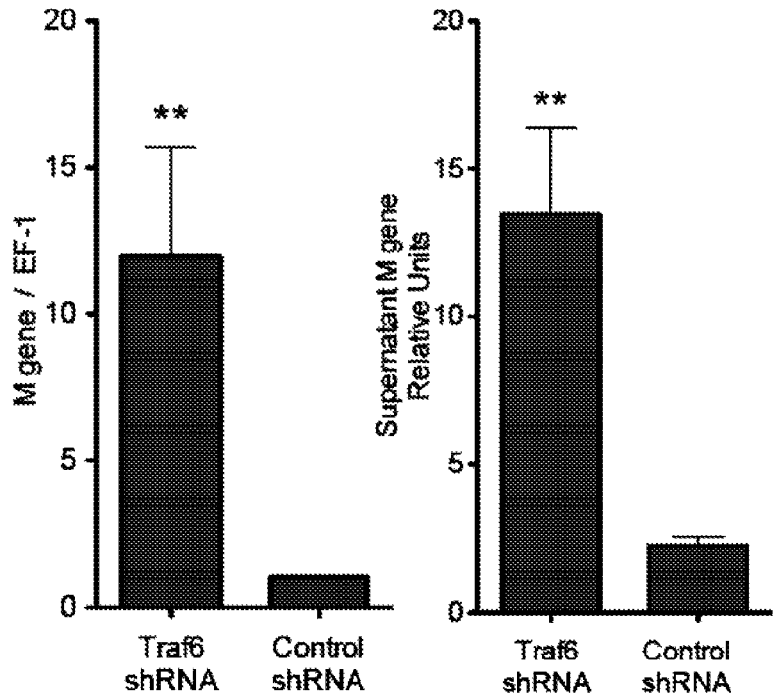

The role of TRAF6 as the proximal component in the TRAF6-IRF7-IFN antiviral network is further reinforced by the observation that decreased TRAF6 levels brought about by two independent approaches (enhanced miR-144 (FIGS. 1B-E) or anti-TRAF6 shRNA (FIGS. 5C-5D)) are associated with significantly increased viral replication. Influenza viral load in SAECs expressing TRAF6-specific or control shRNAs was quantified by qRT-PCR of M gene and normalized to EF-1, with quantities at 18 hours normalized to the initial infection level in each cell type at 1 hour to permit comparison between experiments. Released virus was quantified by measuring viral M gene in the cell-free supernatants 18 hours post-infection. Means±SEM for 3 independent experiments performed in duplicate are shown in FIG. 5C.

Figure 5D:
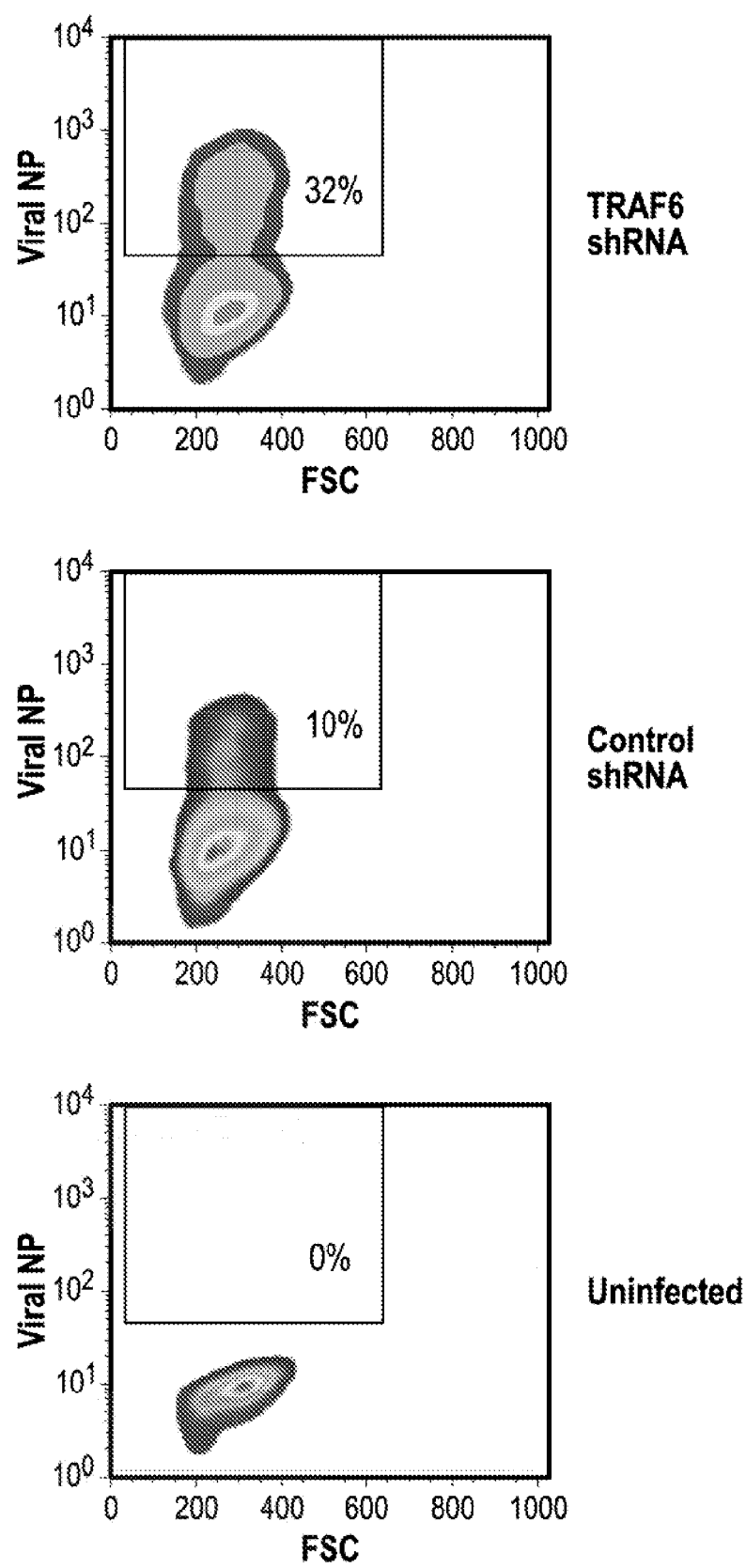

Cells infected as described above were stained for viral NP protein and analyzed by flow cytometry. Again, cells were stained for N protein using antibodies and the cells contained in the boxed portion are those producing N protein. Uninfected cells, of course, do not produce N protein and cells where TRAF6 has been diminished show enhanced expression of the viral protein. Data in FIG. 5D are representative of 2 independent experiments.

The TRAF6-NF-κβ pathway is unaffected by miR-144 under our experimental conditions, despite the fact that TRAF6 can also activate NF-κβ. This is concordant with the observation that the TRAF6-IRF7 pathway can be quantitatively uncoupled from the TRAF6-NF-κβ pathway (Uematsu, S., et al., *J. Exp. Med.* (2005) 201:915). These data support the network model where miR-144 suppresses expression of the TRAF6-IRF7-IFN regulated gene expression network to diminish the antiviral capacity of infected cells.

Example 4

NF-kB Activity is Not Affected by miR-144

Figure 6A:
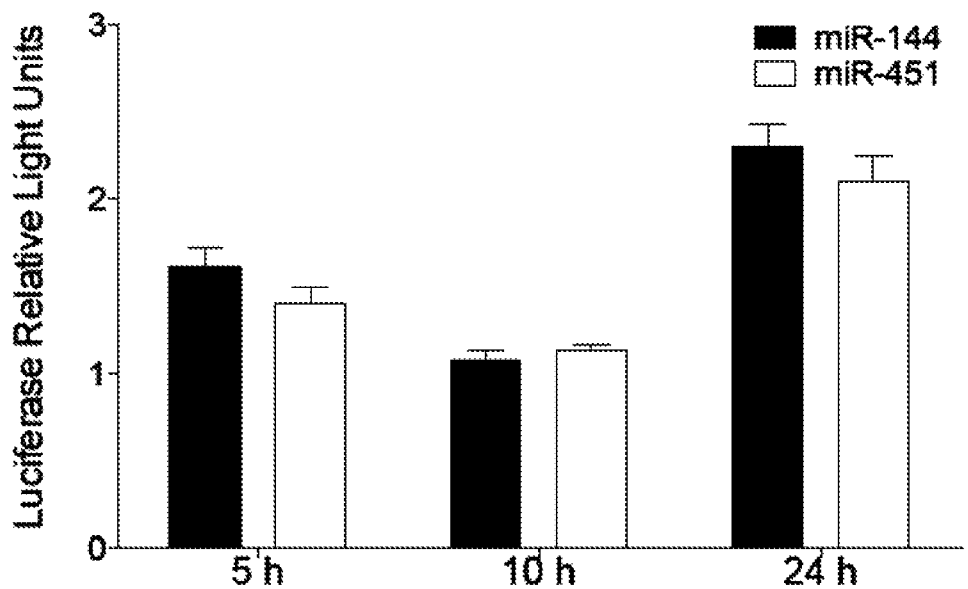
FIGS. 6A-6B show the results of experiments demonstrating that NF-κβ activity is not affected by miR-144.

TC-1 lung epithelial cells were co-transfected with a luciferase reporter plasmid (expressing Renilla luciferase and either NF-κβ or MCMV binding sites upstream of Firefly luciferase) and either miR-144 or miR-451. After 48 h, cells were infected with influenza PR8, cell lysates prepared at the indicated times, and the luminescence from firefly luciferase was quantified relative to Renilla luciferase. Data in FIG. 6A represents 3-4 independent transfections in 2 separate experiments.

Figure 6B:
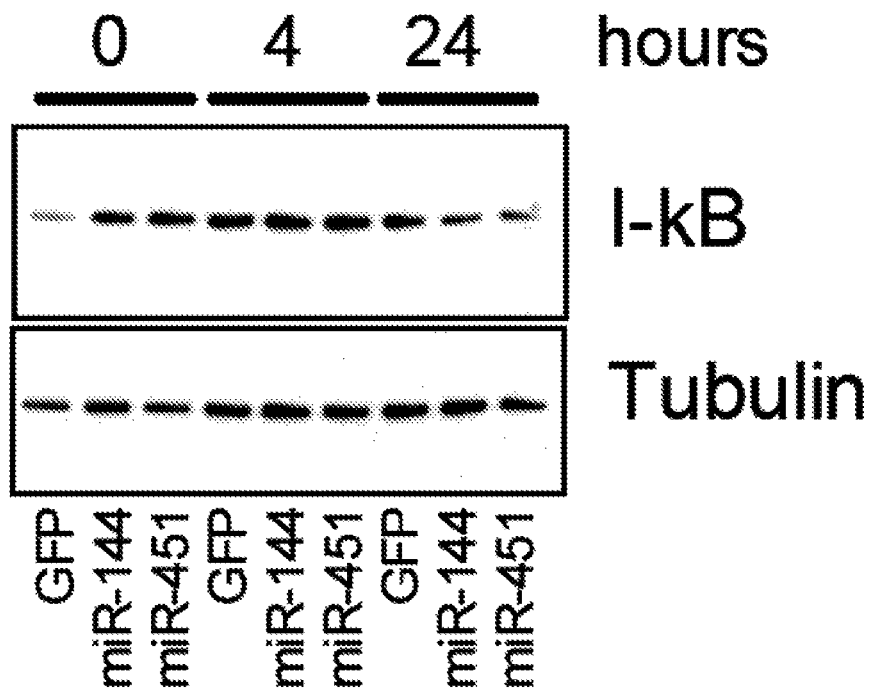

Cell lysates were prepared from influenza-infected SAEC cells after 24 h. Western blots were prepared and probed using antibodies specific for the indicated proteins, and equivalent I-κβ degradation was observed. Data in FIG. 6B is representative of 3 independent experiments.

Figure 6C:
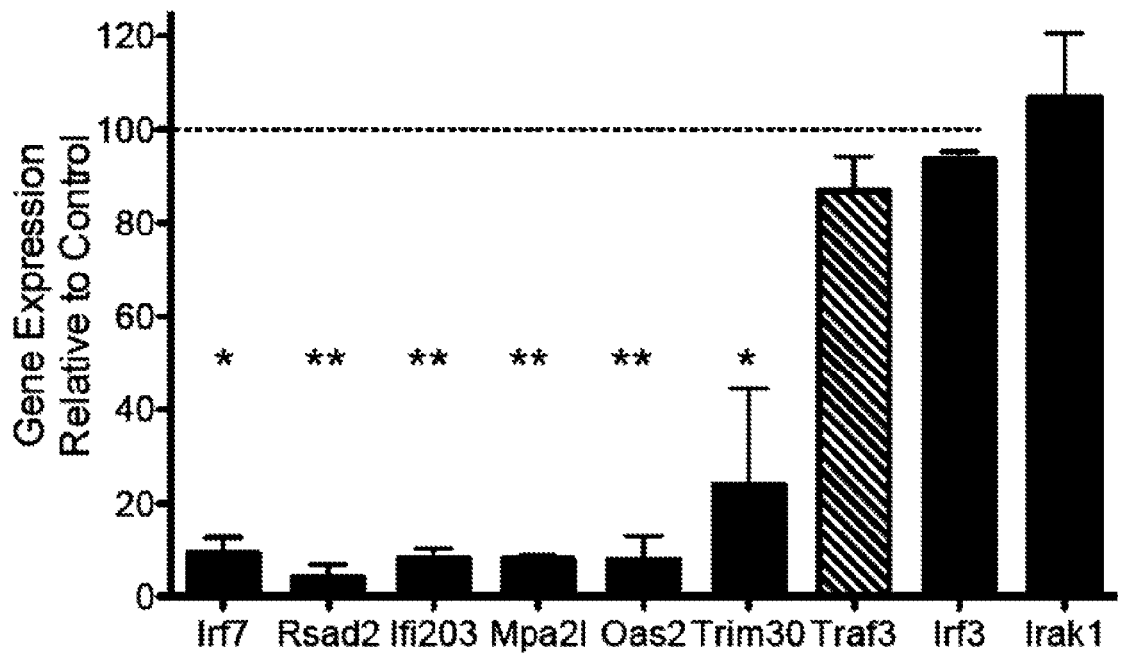
FIG. 6C shows the results on gene expression of controlling the levels of TRAF6 in TC-1 cells and SAEC cells.
Figure 6C:
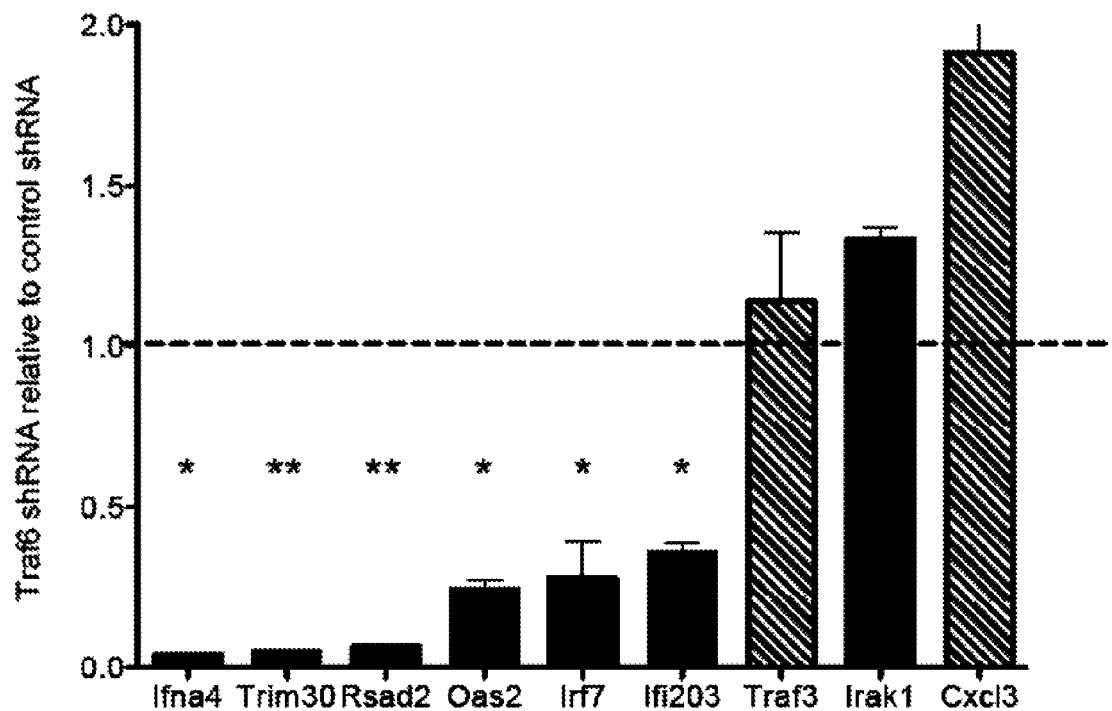

Quantitative RT-PCR was performed on RNA isolated from cells infected for 24 hours and the gene expression level in TC-1 cells expressing miR-144+miR-451 or primary SAEC cells expressing miR-144 alone is shown as a percentage of the level in the relevant vector-only control cells. TRAF3 and CXCL3 are canonical NF-κB-regulated genes, shown by hatched bars. CXCL3 was below the detection limit in TC-1 cells. Data in FIG. 6C represent n=3-8.

Figure 7A:
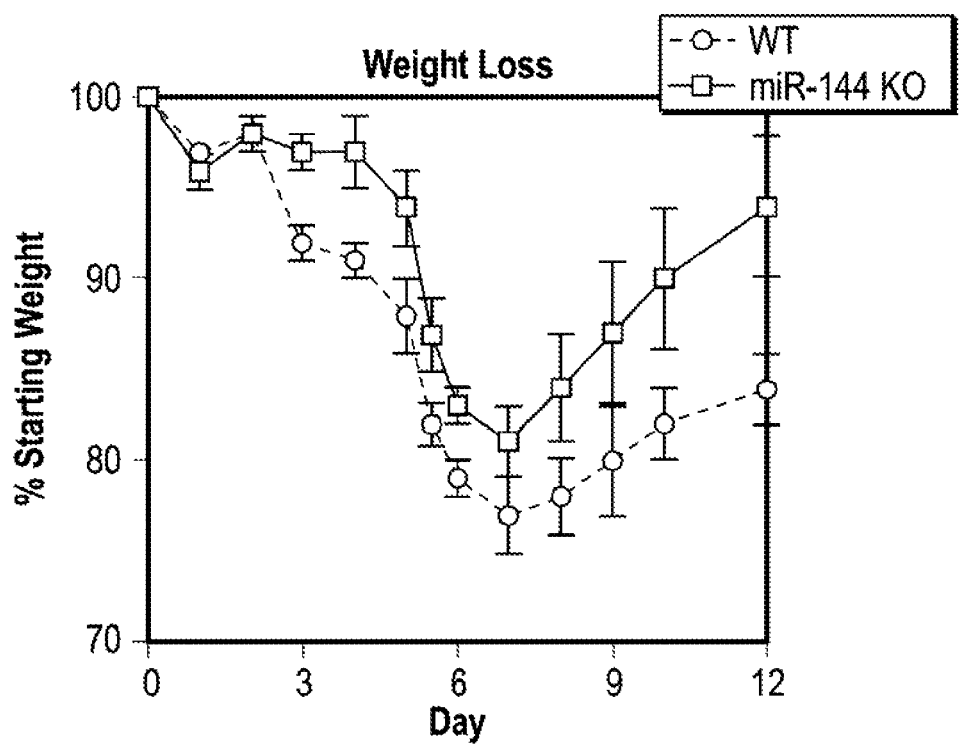
FIGS. 7A-7D show the ability of knock-out (KO) mice that do not produce miR-144 to resist viral infection based on a variety of measures, including weight loss, viral load, and viral gene expression.

Example 5 miR-144/451 Null Mice Show Decreased Morbidity, Decreased Inflammatory White Blood Cell Populations, and Reduced Lung Viral Load Following Influenza Infection Mice were infected intranasally with 700 pfu Influenza A PR8 and weighed daily. Weight loss is graphed in FIG. 7A as a percentage of starting weight and represents 4-13 mice per genotype.

Figure 7B:
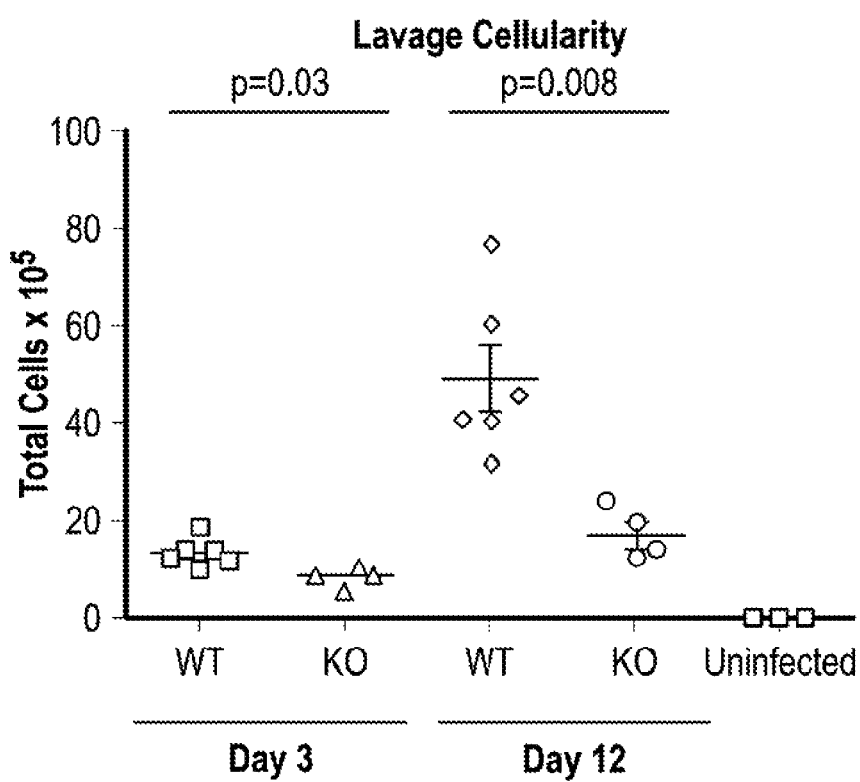

Lung lavage fluid was collected from mice infected as described above at 3 days or 12 days post-infection. Total white blood cell counts from 4-6 mice per time point are shown in FIG. 7B.

Figure 7C:
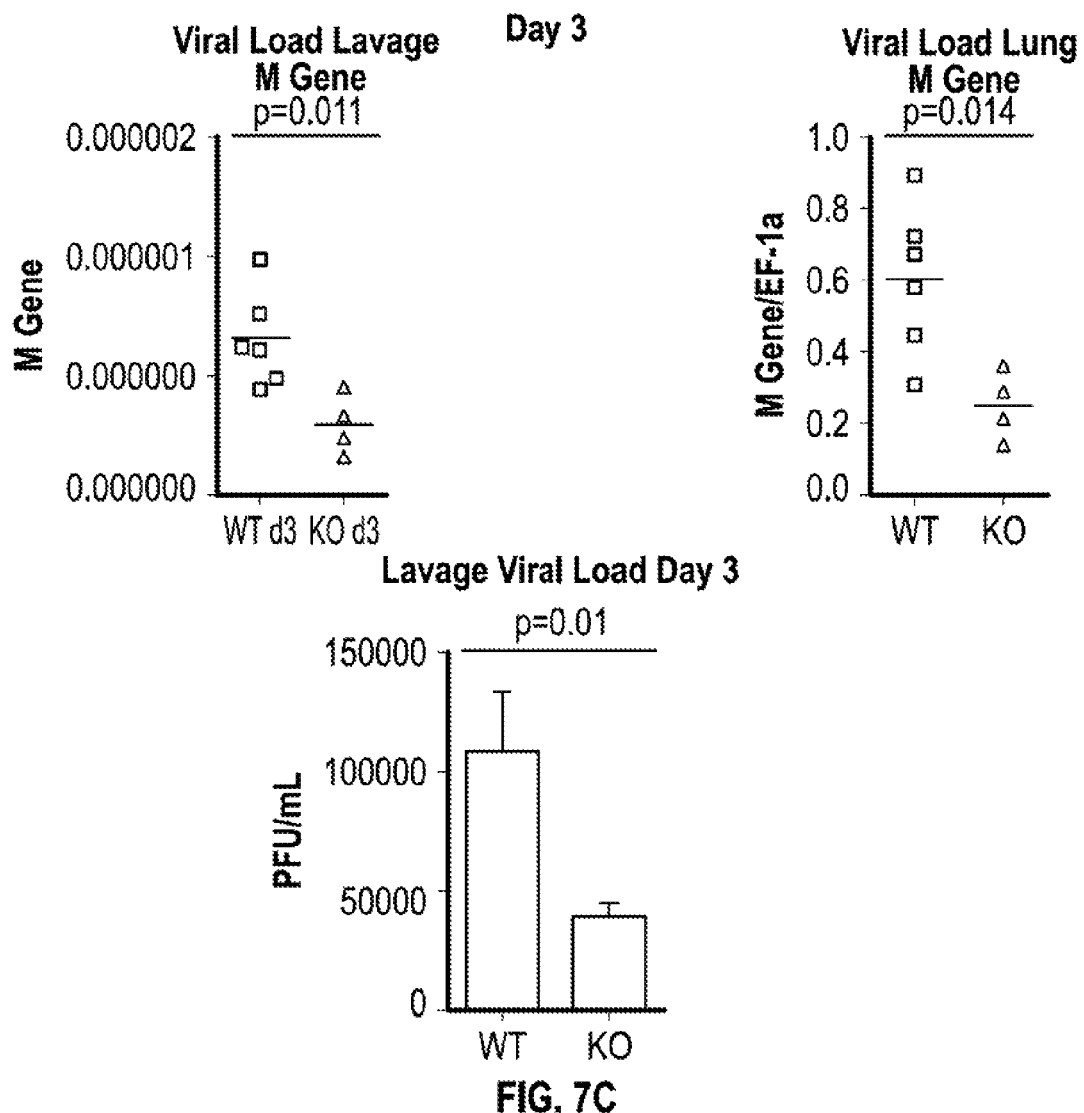

Lung viral load was quantified by qRT-PCR of viral M gene and normalized to host EF-1 in miR-144/miR-451−/− or wild type mice following intranasal infection with influenza for 3 days. Viral load in lung lavage fluid was quantified by qRT-PCR of viral M gene levels in equal volumes of lavage fluid or by plaque-forming unit assay 3 days post-infection as shown in FIG. 7C. Means are shown for 4-6 mice per group.

Figure 7D:
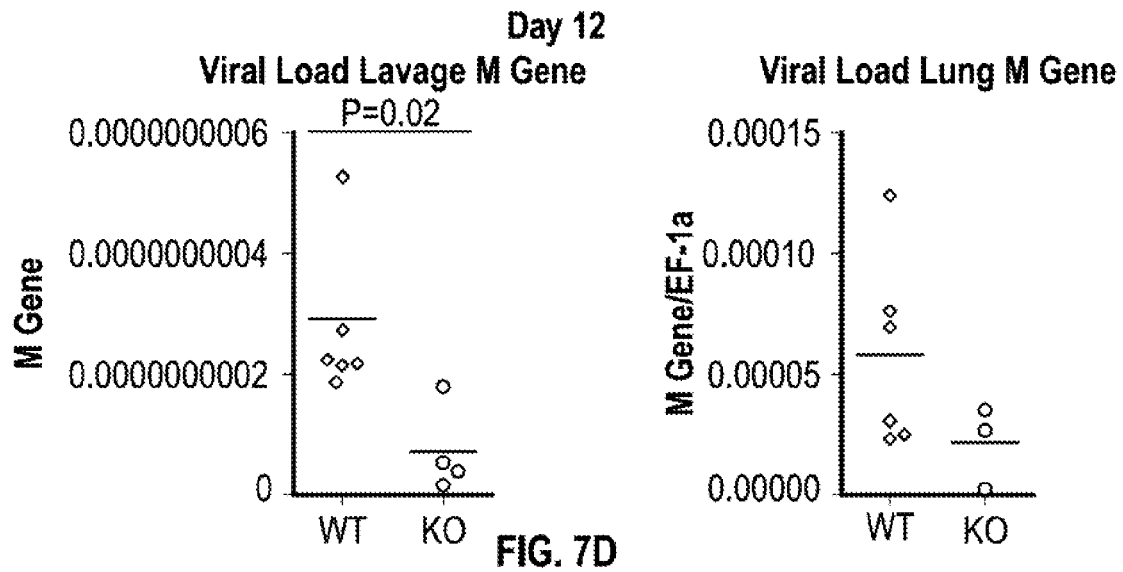

Lung viral load was quantified by qRT-PCR of viral M gene and normalized to host EF-1 in miR-144/miR-451−/− or wild type mice following intranasal infection with influenza for 12 days. Viral load in lung lavage fluid was quantified by qRT-PCR of viral M gene levels in equal volumes of lavage fluid 12 days post-infection as shown in FIG. 7D. Means are shown for 4-6 mice per group.

Example 6

Figure 8A:
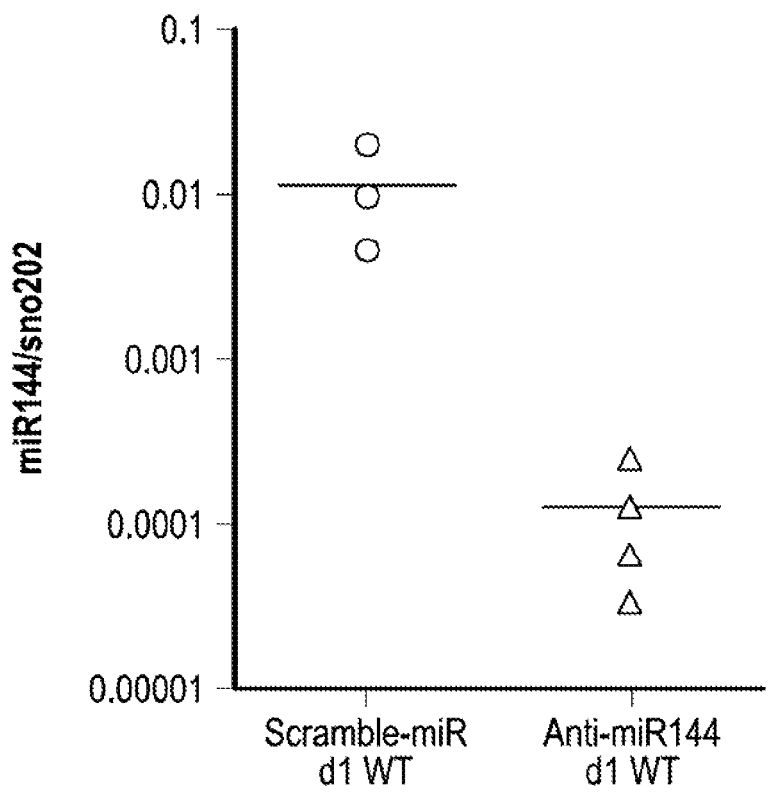
FIGS. 8A-8B show decreased expression of miR-144 inhibits viral infection in mice.

Intranasal Delivery of Antisense miR-144 Oligos to the Lung Effectively Reduces Lung miR-144 Expression and Decreased Influenza A Viral Load LNA-stabilized RNA antisense anti-miR-144 antagomirs or control scramble-miRs (Exiqon) were introduced into the mouse lung by intranasal administration at a concentration of 1-30 mg/kg in 30 µL PBS. Mice were treated 2 days prior to infection and again on the day of infection with Influenza A. This treatment decreased miR-144 levels by 100-fold, as measured by miR-144 expression in mouse lungs as quantified by quantitative RT-PCR and normalization to the expression of sno202 1 day post-infection as shown in FIG. 8A. Decreased microRNA expression in LNA-antagomir-treated mice was observed 5 days following the last administration of anti-miR.

Figure 8B:
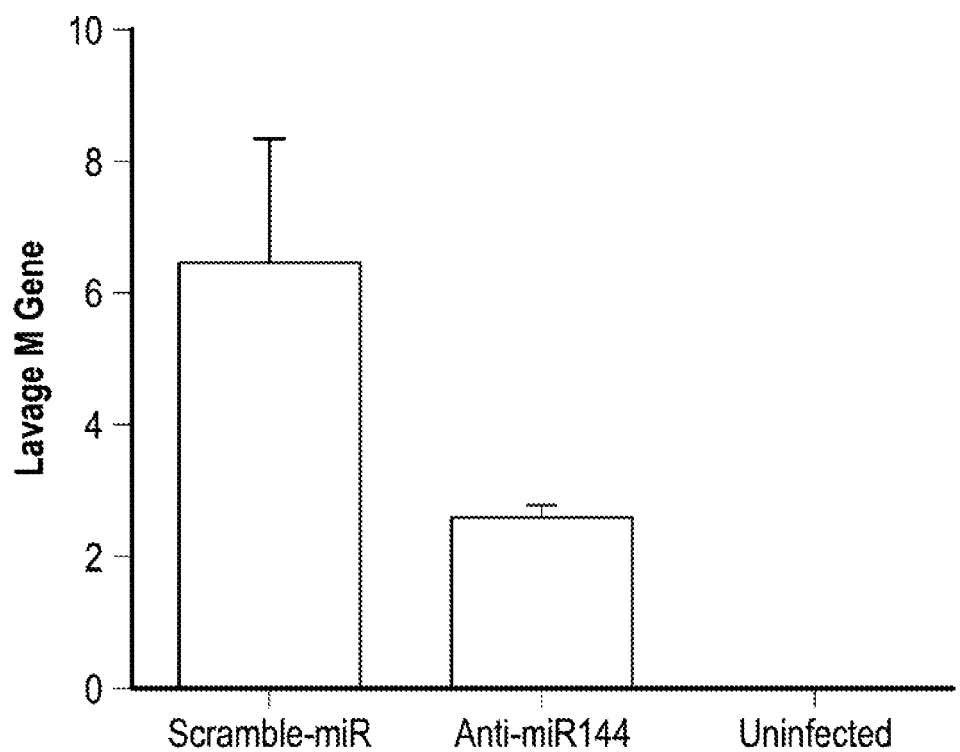

Viral load in the lung lavage of mice treated as described in A were measured 2 days following intranasal infection with Influenza PR8. Reduced miR-144 levels correlated with lower levels of influenza virus in the lung lavage fluid as shown in FIG. 8B.

Example 7

Intranasal Delivery of Antisense miR-144 Oligos to the Lung Effectively Increased Expression of the TRAF6-IRF7-Antiviral Gene Expression Program in Influenza-Infected Lungs LNA-stabilized RNA antisense anti-miR-144 antagomirs or control scramble-miRs (Exiqon) were introduced into the mouse lung by intranasal administration at a concentration of 1-30 mg/mL in 30 µL PBS. Mice were treated 2 days prior to infection and again on the day of infection with Influenza A. There was an increased expression of the module of TRAF6-

Figure 9:
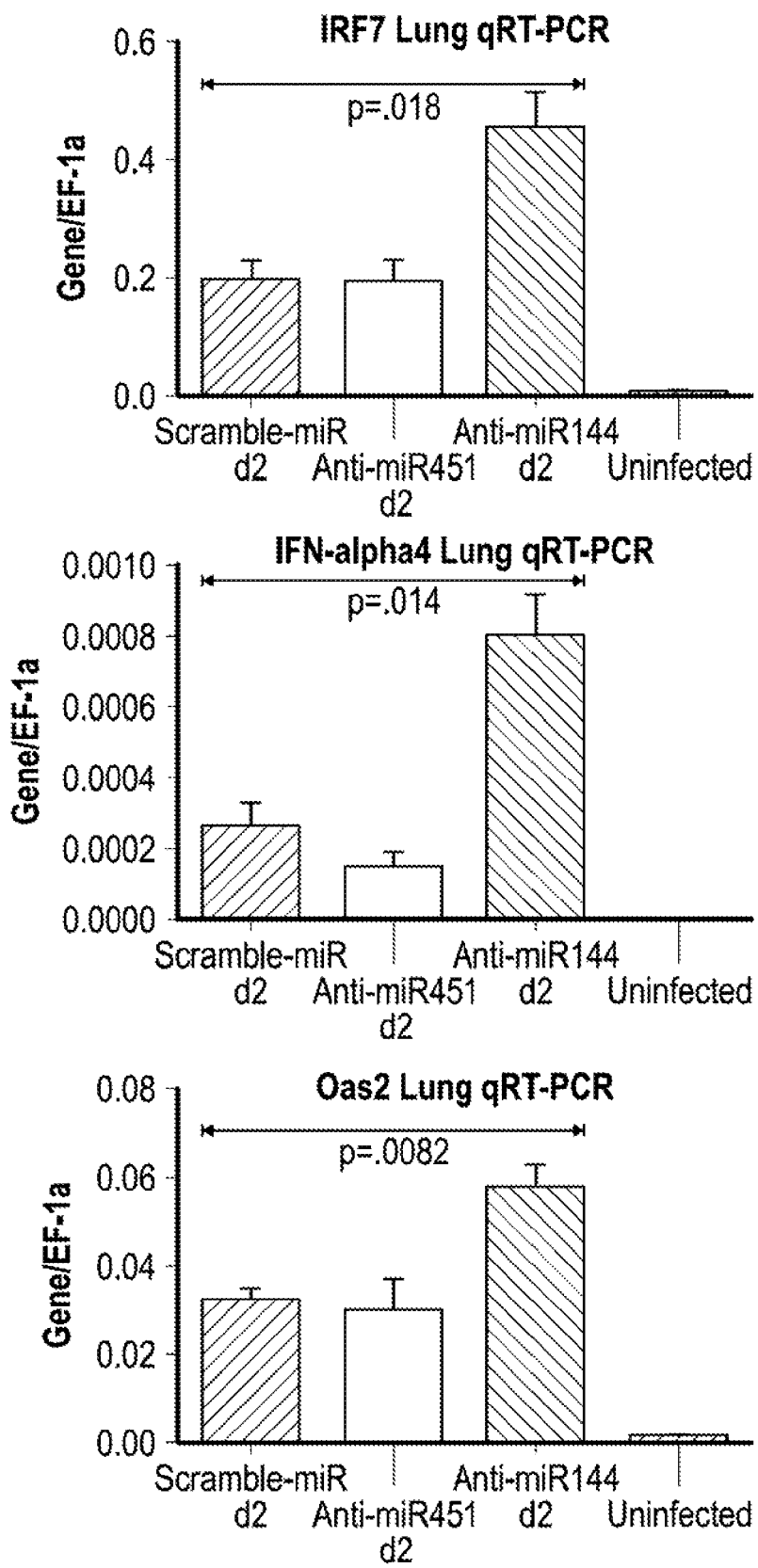
FIG. 9 is a series of graphs showing levels of gene expression of TRAF6-IRF7 controlled antiviral genes in mice treated with antisense LNA anti-miR-144 RNA oligos.
Figure 9:
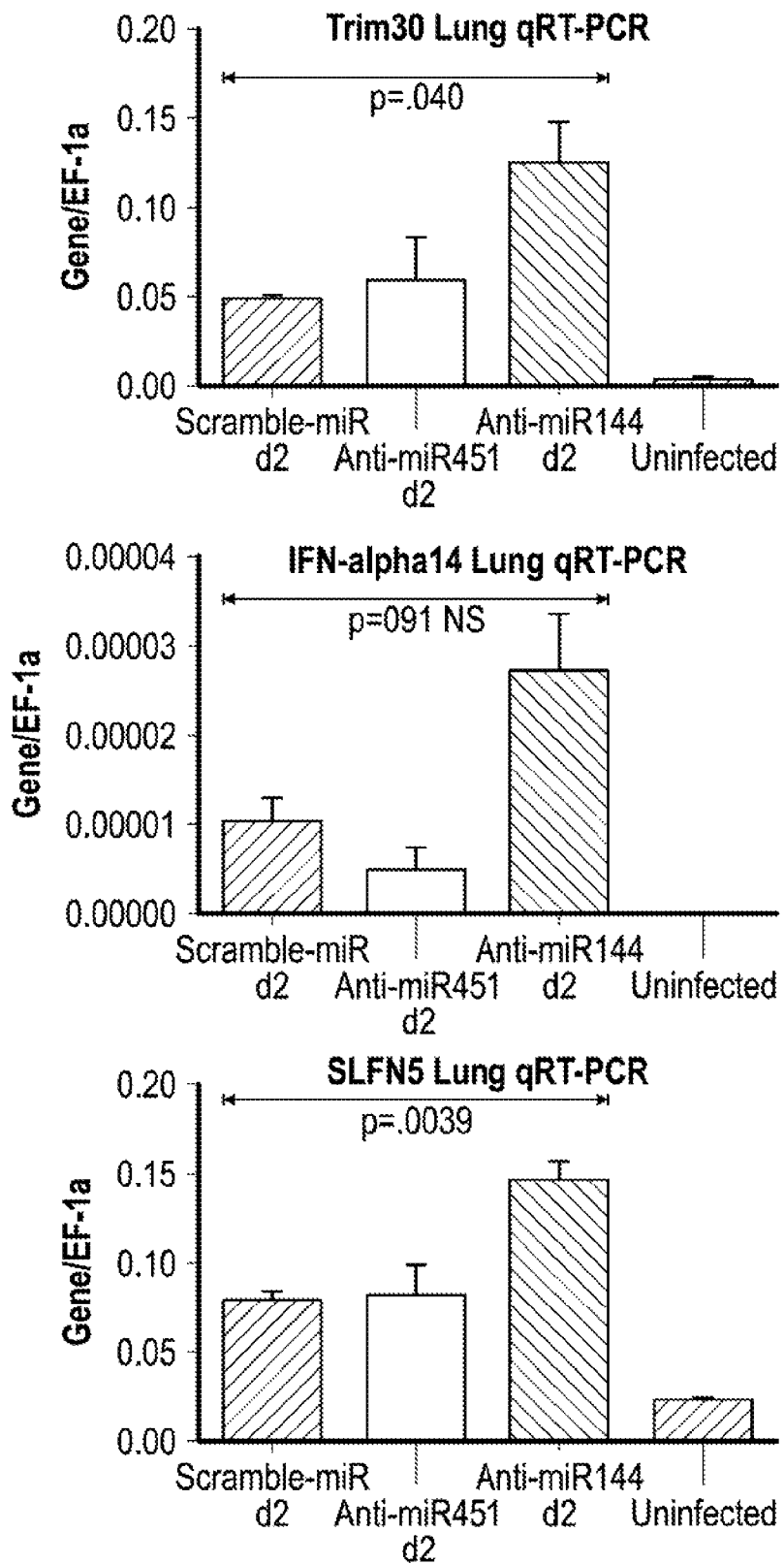
Figure 9:
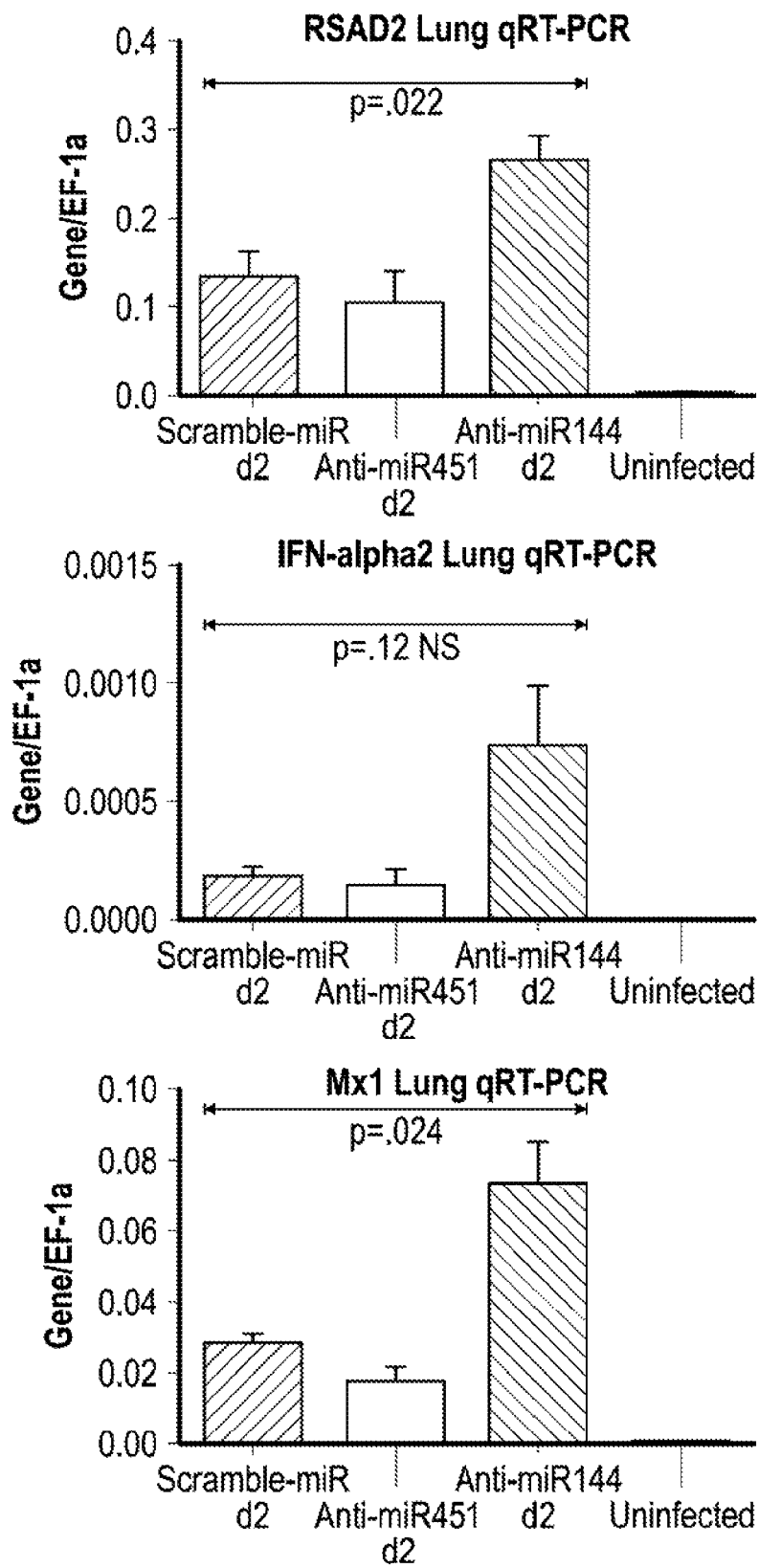
Figure 9:
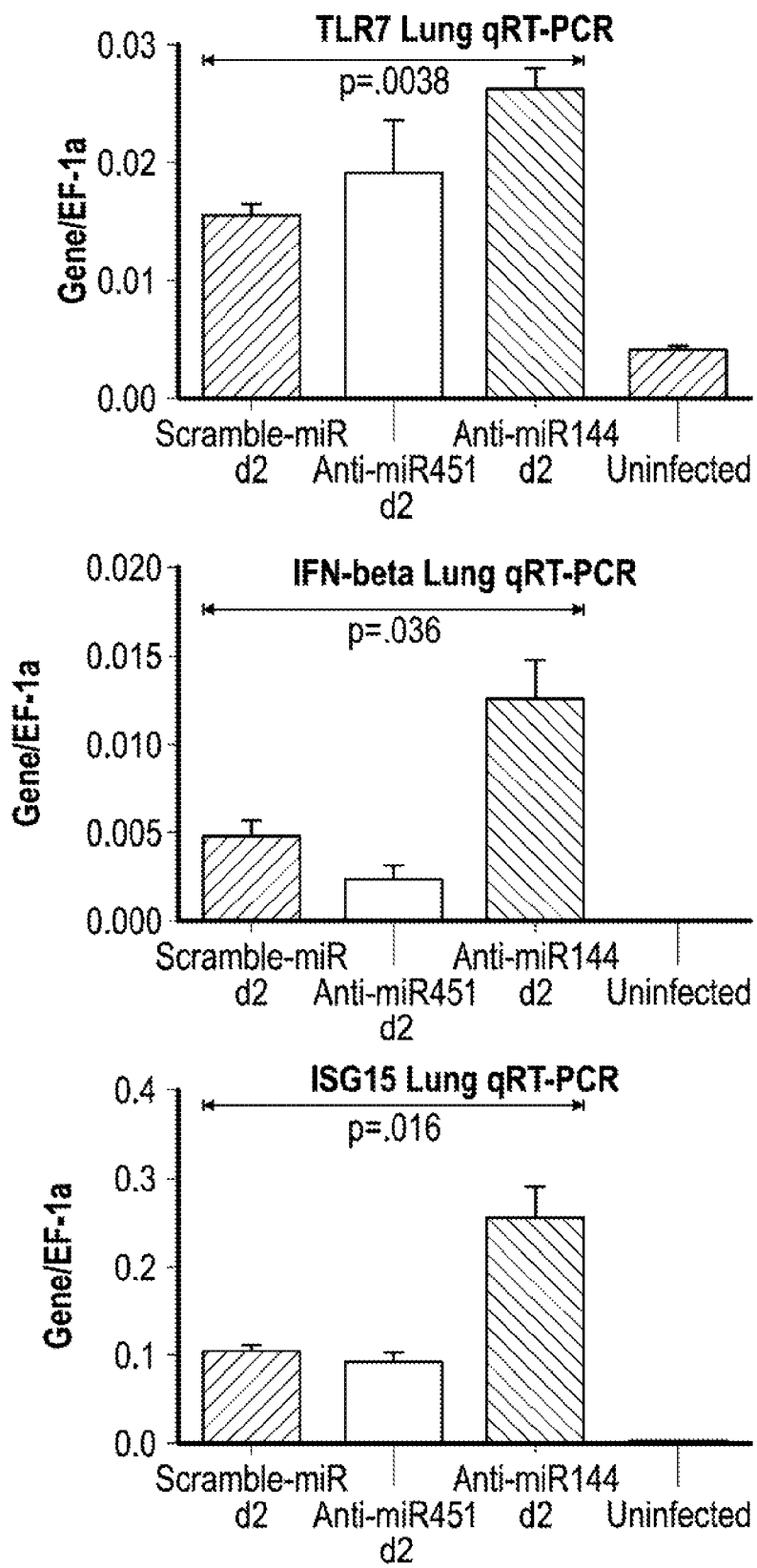
Figure 9:
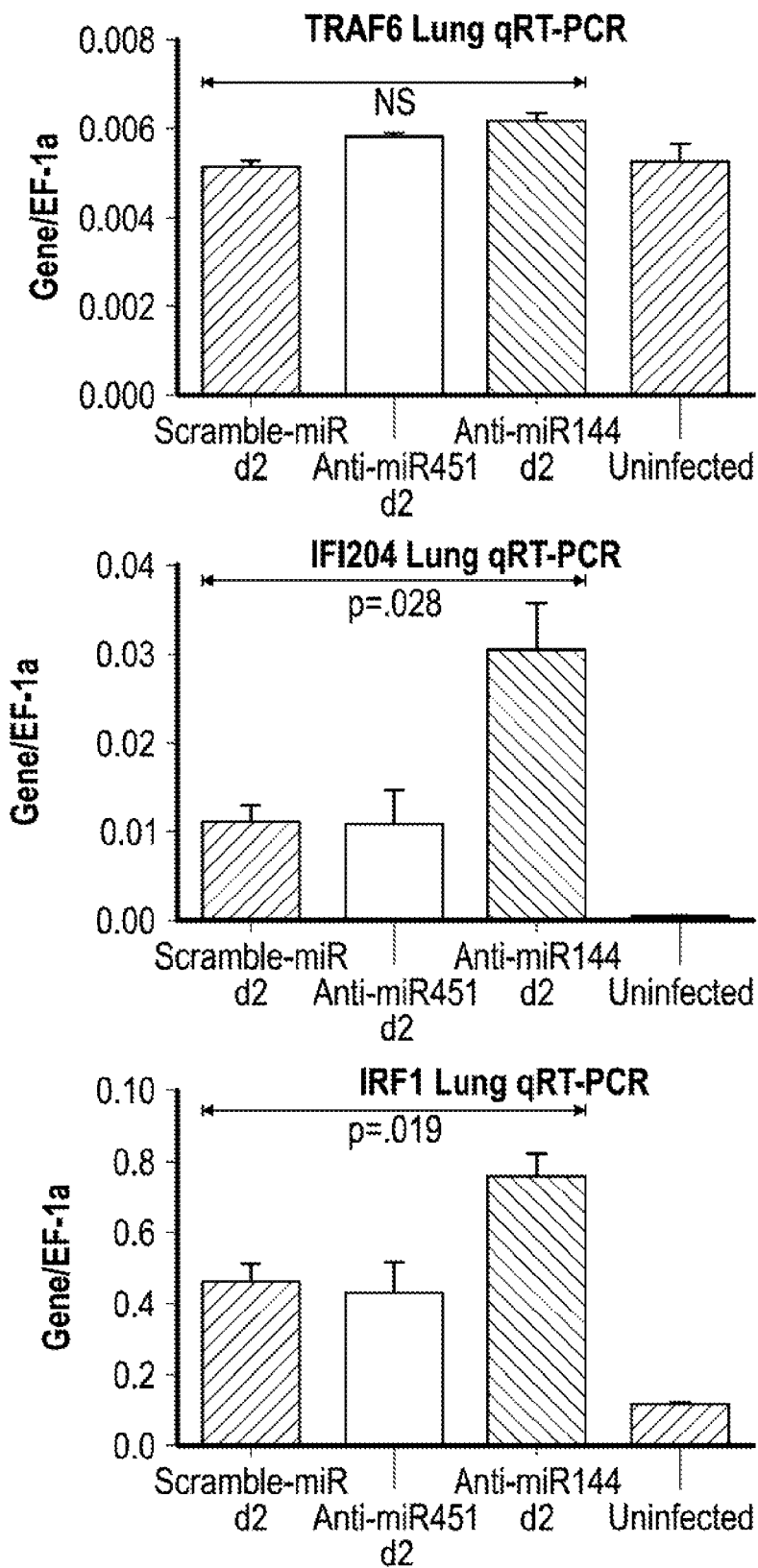

IRF7-antiviral genes predicted by our in vitro data (FIG. 9) in mice treated with antisense LNA anti-miR-144 RNA oligos, when compared with 2 control oligos (anti-miR-451 and scramble-miR). Lung gene expression was measured by quantitative RT-PCR and normalized to EF-1 gene expression levels.

Example 8

Preparation of Antiviral Vaccines

Small airway type I epithelial cells (SAEC) and lung epithelial cells of the TC-1 cell line were modified to overexpress miR-144, miR-451 or vector alone. Constructs expressing both murine miR-144 and miR-451 were cloned with 145 bp upstream of pre-miR-144 and 330 bp downstream from the end of pre-miR-451. miR-451 alone was expressed with flanking sequences 100 bp upstream and 198 bp downstream. miR-144 was cloned with 145 bp upstream of pre-miR-144 and 198 bp downstream of the end of pre-miR-451; the activity of miR-451 included in this construct was ablated using site-directed mutagenesis of 7 bp of the mature miR-451. These sequences were cloned into retroviral MSCV-GFP or lentiviral pLenti6 (±GFP) vectors. Packaged virus was transduced into the indicated cells, and stably selected using 4 μg/mL puromycin (TC-1) or 2 μg/mL puromycin (SAEC cells). Stable cell lines were obtained in each case from these transfections.

The cells were then infected with influenza virus. Cells were infected with influenza at a multiplicity of infection (MOI) of 5 for 1 h in Opti-MEM® in the absence of trypsin, the inoculum removed by washing, and cells cultured in Opti-MEM® for 18-24 h. RNA was collected at 1 h using TRIzol® to quantify initial viral load and RNA, protein, and cell supernatants were collected after 18-24 h. Where indicated, type I interferons were blocked using neutralizing antibodies (RMMA-1 and RMMA-2, PBL) Viral RNA was quantified by RT-PCR using primers specific for influenza M gene (Forward 5' CAT GGA ATG GCT AAA GAC AAG ACC (SEQ ID NO:1), Reverse 5' CCA TTA AGG GCA TTT TGG ACA (SEQ ID NO:2), Probe FAM-5' TTT GTG TTC ACG CTC ACC GTG CCC A-TAMRA (SEQ ID NO:3)) and normalized to the level of mouse EF-1a or human GAPDH or RNA obtained from equivalent volumes of supernatants. To permit comparison between experiments, viral load at 24 h was normalized to initial viral load at 1 h where indicated.

When the cells were cultured, it was shown after 24 hours that in TC-1 cells, ectopic expression of miR-144 significantly increased the load of viral genomes as measured by M gene (FIG. 1C). This phenotype was also observed in immortalized murine primary small airway type I epithelial cells (SAEC) using quantitative RT-PCR for viral genomes.

Primary mouse small airway epithelial cells (SAEC) were immortalized while being transduced with retrovirus expressing miR-144 or miR-451. Cells were infected for 18 hours and M gene measured as described above, and means±SEM are shown (n=6) and results confirmed in 5 independent experiments. Virus released from cells was quantified as shown in FIG. 1D by measuring M gene in the cell supernatants of miR-144-expressing cells relative to miR-451-expressing cells (n=7).

SAECs were infected as described and the percentage of influenza NP positive cells quantified by flow cytometry as in FIG. 1E. The unfilled dotted line represents data from stained uninfected cells. Data are representative of 5 independent experiments. Forward scatter (FSC).

When influenza virus was used as the infective agent, a 10-fold increase in production occurred in the presence of overexpressed of miR-144 and a 7-fold increase in virus count was displayed in cells expressing miR-144 with respect to vesicular stomatitis virus (VSV) and a 50-fold increase in encephalomyocarditis virus (ECMV) was found.

Similar results were obtained in human cells that had been modified to overexpress miR-144.

These results are also shown in Example 1.

The virus is recovered from the cells and further treated to make it suitable for use in vaccines. Means for doing this are known in the art and include inactivation and isolation of relevant components. Alternatively attenuated virus may be used. The resultants are then formulated using standard vaccine techniques such as appropriate solutions for injection or formulated into oral vaccines analogous to the Salk vaccine for polio.

The invention claimed is:

1. A method to product virus for use as a component in an antiviral vaccine, which method comprises:
- modifying host cells that are susceptible to infection by said virus to overexpress miR-144;
- infecting said modified host cells with said virus;
- culturing said infected host cells; and
- recovering virus from the cells.

2. The method of claim 1 which further includes inactivating the recovered virus and/or isolating a desired vaccine component from the recovered virus.

3. The method of claim 1 wherein the virus is attenuated.

4. The method of claim 1 wherein the host cells are epithelial cells.

* * * * *

```
SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: forward primer

<400> SEQUENCE: 1
catggaatgg ctaaagacaa gacc                                             24

<210> SEQ ID NO 2
<211> LENGTH: 21
<212> TYPE: DNA
<213> ORGANISM: Artificial Sequence
<220> FEATURE:
<223> OTHER INFORMATION: reverse primer

<400> SEQUENCE: 2
ccattaaggg cattttggac a                                                21
```

<210> SEQ ID NO 3
<211> LENGTH: 25
<212> TYPE: DNA
<213> ORGANISM: Artificial Sequence
<220> FEATURE:
<223> OTHER INFORMATION: probe

<400> SEQUENCE: 3
tttgtgttca cgctcaccgt gccca                                            25

<210> SEQ ID NO 4
<211> LENGTH: 40
<212> TYPE: DNA
<213> ORGANISM: Artificial Sequence
<220> FEATURE:
<223> OTHER INFORMATION: synthetic construct

<400> SEQUENCE: 4
ttttgtccgt gtactttact gtaaaaaagg ccagacttag                            40

<210> SEQ ID NO 5
<211> LENGTH: 20
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<223> OTHER INFORMATION: miR-144

<400> SEQUENCE: 5
ucauguagua gauaugacau                                                  20

<210> SEQ ID NO 6
<211> LENGTH: 40
<212> TYPE: DNA
<213> ORGANISM: Artificial Sequence
<220> FEATURE:
<223> OTHER INFORMATION: synthetic construct

<400> SEQUENCE: 6
ttttgtccgt gtacttcgaa tcgaaaaagg ccagacttag                            40

<210> SEQ ID NO 7
<211> LENGTH: 40
<212> TYPE: DNA
<213> ORGANISM: Artificial Sequence
<220> FEATURE:
<223> OTHER INFORMATION: synthetic construct

<400> SEQUENCE: 7
cactgcatgg tcttatactg tagttgtttc ccagtggagg                            40

<210> SEQ ID NO 8
<211> LENGTH: 40
<212> TYPE: DNA
<213> ORGANISM: Artificial Sequence
<220> FEATURE:
<223> OTHER INFORMATION: synthetic construct

<400> SEQUENCE: 8
cactgcatgg tcttacgaat cggttgtttc ccagtggagg                            40